United States Patent
Castex

(10) Patent No.: US 11,338,023 B2
(45) Date of Patent: May 24, 2022

(54) COMPOSITIONS AND METHODS FOR MODULATING AND/OR STIMULATING IMMUNE RESPONSES IN HUMAN AND/OR ANIMAL

(71) Applicant: DANSTAR FERMENT AG, Zug (CH)

(72) Inventor: Mathieu Castex, Blagnac (FR)

(73) Assignee: DANSTAR FERMENT AG, Zug (CH)

( * ) Notice: Subject to any disclaimer, the term of this patent is extended or adjusted under 35 U.S.C. 154(b) by 0 days.

(21) Appl. No.: 15/741,832

(22) PCT Filed: Jul. 11, 2016

(86) PCT No.: PCT/EP2016/066446
§ 371 (c)(1),
(2) Date: Jan. 4, 2018

(87) PCT Pub. No.: WO2017/005936
PCT Pub. Date: Jan. 12, 2017

(65) Prior Publication Data
US 2018/0207248 A1 Jul. 26, 2018

(30) Foreign Application Priority Data

Jul. 9, 2015 (EP) ..................................... 15176029

(51) Int. Cl.
| | | |
|---|---|---|
| *A61K 39/00* | (2006.01) | |
| *A61K 36/06* | (2006.01) | |
| *A61K 36/064* | (2006.01) | |
| *A23K 50/80* | (2016.01) | |
| *A23K 20/163* | (2016.01) | |
| *A23K 50/75* | (2016.01) | |
| *A23K 50/30* | (2016.01) | |
| *A23K 50/60* | (2016.01) | |
| *A23K 50/20* | (2016.01) | |
| *A61K 31/715* | (2006.01) | |

(52) U.S. Cl.
CPC ........ *A61K 39/0002* (2013.01); *A23K 20/163* (2016.05); *A23K 50/20* (2016.05); *A23K 50/30* (2016.05); *A23K 50/60* (2016.05); *A23K 50/75* (2016.05); *A23K 50/80* (2016.05); *A61K 31/715* (2013.01); *A61K 36/06* (2013.01); *A61K 36/064* (2013.01)

(58) Field of Classification Search
CPC ........ A23V 2002/00; A23V 2200/3202; A23V 2250/51; A23K 20/163; A23K 50/10; A23K 50/20; A23K 50/30; A23K 50/60; A23K 50/75; A23K 50/80; A61K 31/715; A61K 36/06; A61K 36/064; A61K 39/0002

See application file for complete search history.

(56) References Cited

U.S. PATENT DOCUMENTS 5,506,210 A * 4/1996 Parish .................... A61K 31/70
514/23
6,214,337 B1 4/2001 Hayen et al.

FOREIGN PATENT DOCUMENTS

| CN | 102228138 A | 11/2011 |
| EP | 0 466 037 A2 | 1/1992 |
| JP | 2009-203160 A | 9/2009 |
| WO | 96/13571 A1 | 5/1996 |
| WO | WO 2007138781 A1 * | 12/2007 |
| WO | 2008/128972 A1 | 10/2008 |

OTHER PUBLICATIONS

WO 2007138781 A1, Machine translation—Description.*
WO 2007138781 A1, Machine translation—Claims.*
Herbert H. Zeitschrift fur Gastroenterologie, vol. 55, No. 8, pp. 772-778, 2017.*
Bauerrova et al. Neuroendocrinol. Lett. 29: 691-696, 2008.*
Krizkova et al. Mutation Res. 497: 213-222, 2001.*
Kogan et al. Neoplasma 55: 387-393, 2008.*
Paul et al. Indian J. Animal Sci. 83: 307-309, 2013.*
Dimitroglou, A. et al., "Dietary mannan oligosaccharide supplementation modulates intestinal microbial ecology and improves gut morphology of rainbow trout, *Oncorhynchus mykiss* (Walbaum)," J Anim Sci 2009.87:3226-3234.
Jawhara, S. et al., "Modulation of Intestinal Inflammation by Yeasts and Cell Wall Extracts: Strain Dependence and Unexpected Anti-Inflammatory Role of Glucan Fractions," PLoS ONE, Jul. 2012, vol. 7, issue 7, e40648.
Marakalala, M. et al., "Dectin-1: a role in antifungal defense and consequences of genetic polymorphisms in humans," Mamm Genome (2011) 22:55-65.
Sorenson, W.G., et al., "Cell Wall Preparations from Environmental Yeasts: Effect on Alveolar Macrophage Function In Vitro," Ann Agric Environ Med 1998, 5, 65-71.
Vandesompele, J. et al., "Accurate normalization of real-time quantitative RT-PCR data by geometric averaging of multiple internal control genes," Genome Biology 2002, 3(7).

* cited by examiner

*Primary Examiner* — Sarvamangala Devi
(74) *Attorney, Agent, or Firm* — Nixon & Vanderhye

(57) ABSTRACT

There is provided a composition including parietal polysaccharides from at least one *Candida* species and parietal polysaccharides from at least one different yeast species. The composition can be used in modulating and/or stimulating immune responses in animal or human.

15 Claims, 19 Drawing Sheets

FIGURE 11

| Parameter | Control | 60 SC PARIETAL POLYSACCHARIDES | Treatment 50 SC/CU PARIETAL POLYSACCHARIDES (cont.) | 50 SC/CU PARIETAL POLYSACCHARIDES (pulsed) | P-value |
|---|---|---|---|---|---|
| Initial weight (g/fish) | 23.05 ± 0.30 | 23.03 ± 0.20 | 23.12 ± 0.27 | 23.07 ± 0.20 | 0.973 |
| Final weight (g/fish) | 83.33 ± 2.94 | 81.63 ± 2.13 | 80.03 ± 2.05 | 82.22 ± 1.52 | 0.257 |
| Weight gain (g/fish) | 60.28 ± 3.08 | 58.60 ± 2.64 | 56.91 ± 0.34 | 59.15 ± 2.74 | 0.218 |
| FCR (g/g) | 1.00 ± 0.01 | 1.00 ± 0.02 | 1.05 ± 0.05 | 1.03 ± 0.02 | 0.175 |
| SGR (% BW/day) | 2.34 ± 0.04 | 2.34 ± 0.04 | 2.28 ± 0.09 | 2.29 ± 0.06 | 0.156 |
| PER | 1.57 ± 0.03 | 1.55 ± 0.04 | 1.48 ± 0.10 | 1.52 ± 0.04 | 0.220 |
| K – Factor | 1.46 ± 0.09 | 1.38 ± 0.09 | 1.43 ± 0.09 | 1.41 ± 0.07 | 0.092 |

COMPOSITIONS AND METHODS FOR MODULATING AND/OR STIMULATING IMMUNE RESPONSES IN HUMAN AND/OR ANIMAL

FIELD OF THE INVENTION

The present application relates to compositions and methods for modulating and/or stimulating immune responses in human and/or animal.

BACKGROUND OF THE INVENTION

Yeast and its derivatives are increasingly used as a nutritional supplement to improve the intestinal health of animals and humans through activation of anti-fungal immune responses initiated in the intestinal mucosal surface, primarily through Dectin 1 and β-glucan pathways, or via direct binding with undesirable bacteria in the digestive tract. Both effects are dependent on the specificity of immune antigen expression within yeast cell wall and antigen receptor expression within intestinal epithelial cells. However it should be noted that beyond the well described β-glucan/Dectin 1 interaction, other "yeast ligands"-receptors interactions mediating the activation of the immune response, and more specifically of the anti-fungal immune response, may have significant roles and are directly depending on the composition and the structure of the yeast cell wall. There are currently market options using unspecific inactive yeast-based products claiming to stimulate immune responses through these pathways; however these products lack specificity and consistency in terms of composition and outcome. It would be highly desirable to be provided with an improved yeast-based product that would enhance the stimulation of animal or human immune responses.

SUMMARY OF THE DISCLOSURE

The present disclosure provides a composition comprising parietal polysaccharides from at least one *Candida* species and parietal polysaccharides from at least one different yeast species. Surprisingly, the parietal polysaccharides from at least one *Candida* species, when combined with parietal polysaccharides from at least one different yeast species, lead to an enhanced stimulation of animal or human immune responses, even at low inclusion rate. In some embodiments, the parietal polysaccharides from the at least one *Candida* species are in an amount ranging from 1 to 99 dry weight percent based on the total weight of parietal polysaccharides in the composition. In an embodiment, the parietal polysaccharides from at least one *Candida* species are in an amount ranging from 10 to 50 dry weight percent based on the total weight of parietal polysaccharides in the composition. In alternative or complimentary embodiments, the parietal polysaccharides from at least one *Candida* species and parietal polysaccharides from at least one different yeast species are in an amount ranging from 1 to 100 weight percent based on the total weight of the composition. In an embodiment, the parietal polysaccharides from at least one *Candida* species and parietal polysaccharides from at least one different yeast species are in an amount ranging from 20 to 80 weight percent based on the total weight of the composition. In another embodiment, the parietal polysaccharides from at least one *Candida* species and parietal polysaccharides from at least one different yeast species are in an amount ranging from 30 to 60 weight percent based on the total weight of the composition. In an embodiment, the at least one *Candida* species is *Candida utilis*. In another embodiment, the at least one different yeast species is from *Saccharomyces* sp, *Hanseniaspora* sp, *Hansenula* sp, *Kluyveromyces* sp, *Metschnikowia* sp, *Pichia* sp, *Starmerella* sp and *Torulaspora* sp or mixture thereof. The at least one different yeast species also comprises as well as inter-species hybrids derived from any one of these yeast species.

The present disclosure also provides uses of the as defined in the preceding embodiments in modulating and/or stimulating immune responses in animal and/or in human. In another embodiment, the animal is a domestic animal.

The present disclosure also provides a method of modulating and/or stimulating immune responses in animal by administering to an animal a composition comprising parietal polysaccharides from at least one *Candida* species and parietal polysaccharides from at least one different yeast species. In an embodiment, the combination is in a form of a food additive, animal feed or pharmaceutical product. In another embodiment, the pharmaceutical product can be administered orally or parenterally. In yet another embodiment, the food additive, animal feed can be presented in formats that are added to a complete animal or human diet or added separately as tablets, pellets, or beads to be consumed directly. In still another embodiment, the animal is a domestic animal.

BRIEF DESCRIPTION OF THE DRAWINGS

Having thus generally described the nature of the invention, reference will now be made to the accompanying drawings, showing by way of illustration, a preferred embodiment thereof, and in which:

FIG. 11 shows the growth performance in control fed fish and in rainbow trout fed with the experimental diets for 56 days according to example 9.

DETAILED DESCRIPTION

Figure 1:
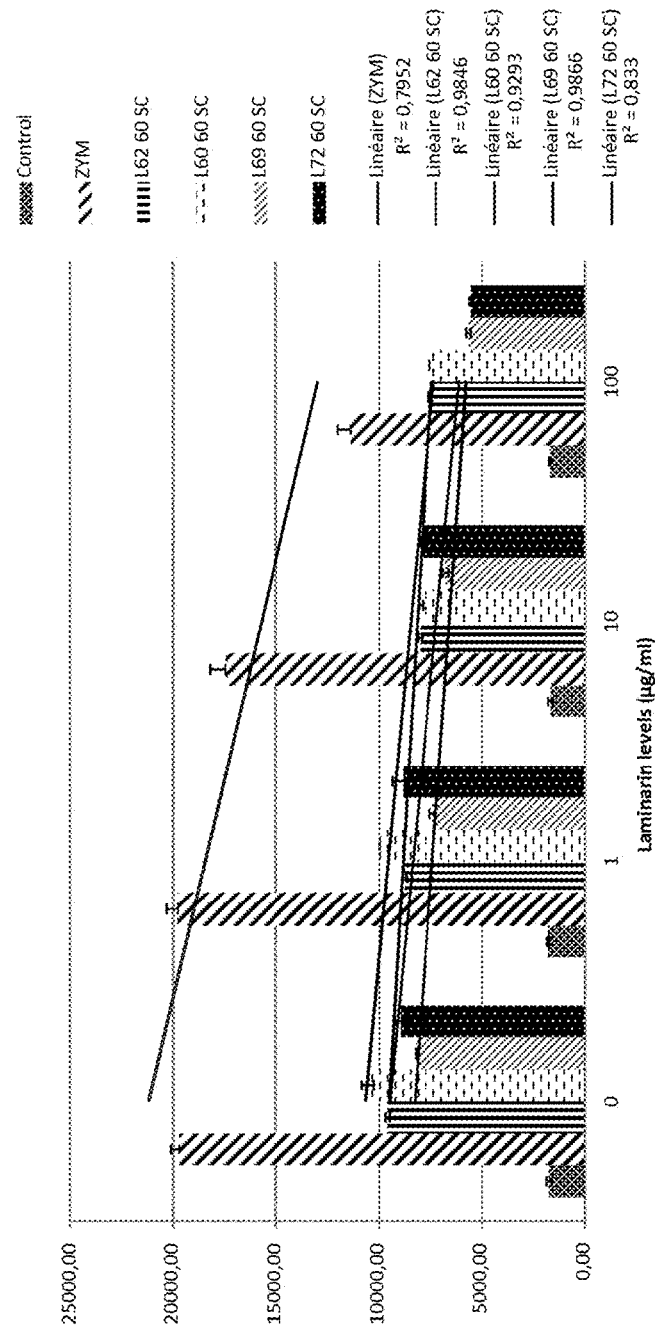
FIG. 1 shows the effect of Laminarin inclusion on the In vitro production of reactive oxygen species (ROS) by monocytes incubated with parietal polysaccharides from different *Saccharomyces cerevisiae* strains according to example 1, assay 1.

The cell walls of fungi consist predominantly of parietal polysaccharides including chitin, mannose-based structure and beta-glucans. Glucans compose up to 50% of the cell wall and are biologically active agents that are used therapeutically to modify immune responses. Experimentally, these parietal polysaccharides can confer protection against a variety of challenges including tumor development and infections. Recently many advances have been made toward understanding host immune response to infections. Novel cell surfaces molecules have been discovered that regulate host response to microorganisms. Those receptors are called Pathogen-associated pattern Recognition Receptors (PRR) and are mainly known as the Toll like receptors, the C type lectin receptors, the scavenger receptors and the complement receptors.

These immune receptors are activated by specific ligands, which are encountered at the surface of bacteria or fungi. In the case of fungi, glucose units connected by β-1,3 and β-1,6 glycosidic linkages, referred as β-glucans, and mainly extracted from *Saccharomyces cerevisiae,* have been shown to induce antimicrobial, fungicidal and anti-tumor activity. The mechanism whereby these molecules induce protection involves immune receptors; one of these is Dectin 1, the major β-glucans receptor on monocytes. It contains a single extracellular C-type lectin-like parietal polysaccharide recognition domain able to recognize yeast cells or derivatives and contributes to the mobilization of the immune response. Thus the C type lectin receptor Dectin 1 is described (Marakala et al., Mamm Genome (2011) 22:55-65) to bind beta-glucans from *Saccharomyces cerevisiae* and to be involved in the induction of various pathways leading notably to the phagocytosis and elimination of particles such as the zymosan, a cell wall extract from *Saccharomyces cerevisiae,* and other yeast derivatives obtained from strains of *Saccharomyces cerevisiae* (examples of other yeast derivatives are, but not limited to, yeast cell wall, inactive yeasts or autolyzed yeast). Threat detection mechanisms and the immediate responses to infection are highly conserved and immune responses are triggered partly by the binding of these pathogen ligands, for example the beta-glucans, to PRRs on the surface of host cells. Within hours, the non-specific innate immune system is activated, associated with an inflammation. Local Inflammation plays an important role in this immediate response to infection. Numerous players in the innate immune system, including neutrophils, monocytes, macrophages, complement factors, cytokines, antimicrobial peptides and acute phase proteins, are mobilized rapidly in a complex and highly regulated response to provide immediate defense against infection. There are currently market options for inactive yeast-based products that claim to stimulate immune responses through these pathways; however these products lack specificity and consistency in outcome. It would be highly desirable to be provided with an improved yeast-based product that would enhance the stimulation of animal or human immune responses.

The present disclosure provides a composition comprising parietal polysaccharides from at least one *Candida* species and parietal polysaccharides from at least one different yeast species. In the context of the present disclosure, a "parietal polysaccharides" are chitin, Mannan-oligosaccharides, Beta 1,3 glucans and Beta 1,6 glucans. Surprisingly, the parietal polysaccharides from at least one *Candida* species, when combined with parietal polysaccharides from at least one different yeast species, lead to an enhanced stimulation of animal or human immune responses, even at low inclusion rate.

In some embodiments, the parietal polysaccharides from the at least one *Candida* species are in an amount ranging from 1 to 99 dry weight percent based on the total weight of parietal polysaccharides in the composition. In an embodiment, the parietal polysaccharides from at least one *Candida* species are in an amount ranging from 5 to 90 dry weight percent based on the total weight of parietal polysaccharides in the composition. In another embodiment, the parietal polysaccharides from at least one *Candida* species are in an amount ranging from 5 to 80 dry weight percent based on the total weight of parietal polysaccharides in the composition. In yet another embodiment, the parietal polysaccharides from at least one *Candida* species are in an amount ranging from 10 to 75 dry weight percent based on the total weight of parietal polysaccharides in the composition. In still another embodiment, the parietal polysaccharides from at least one *Candida* species are in an amount ranging from 10 to 60 dry weight percent based on the total weight of parietal polysaccharides in the composition. In an embodiment, the parietal polysaccharides from at least one *Candida* species are in an amount ranging from 10 to 50 dry weight percent based on the total weight of parietal polysaccharides in the composition. In another embodiment, the parietal polysaccharides from at least one *Candida* species are in an amount ranging from 10 to 20 dry weight percent based on the total weight of parietal polysaccharides in the composition. In yet another embodiment, the parietal polysaccharides from at least one *Candida* species are in an amount ranging from 10 to 15 dry weight percent based on the total weight of parietal polysaccharides in the composition. In still a further embodiment, the parietal polysaccharides from at least one *Candida* species are in an amount of at least 10, 15, 20, 25, 30, 35, 40, 45 or 50 dry weight percent based on the total weight of parietal polysaccharides in the composition. In another embodiment, the parietal polysaccharides from at least one *Candida* species are in an amount of at least 10, 11, 12, 13, 14, 15 16, 17, 18, 19 or 20 dry weight percent based on the total weight of parietal polysaccharides in the composition. In still a further embodiment, the parietal polysaccharides from at least one *Candida* species are in an amount of at least 10, 11, 12, 13, 14 or 15 dry weight percent based on the total weight of parietal polysaccharides in the composition.

In alternative or complimentary embodiments, the parietal polysaccharides from at least one different yeast species are in an amount ranging from 1 to 99 dry weight percent based on the total weight of parietal polysaccharides in the composition. In an embodiment, the parietal polysaccharides from at least one different yeast species are in an amount ranging from 50 to 90 dry weight percent based on the total weight of parietal polysaccharides in the composition. In another embodiment, the parietal polysaccharides from at least one different yeast species are in an amount ranging from 70 to 90 dry weight percent based on the total weight of parietal polysaccharides in the composition. In yet another embodiment, the parietal polysaccharides from at least one different yeast species are in an amount ranging from 80 to 90 dry weight percent based on the total weight of parietal polysaccharides in the composition. In still a further embodiment, the parietal polysaccharides from at least one different yeast species are in an amount of at least 50, 55, 60, 65, 70, 75, 80, 85 or 90 dry weight percent based on the total weight of parietal polysaccharides in the composition. In another embodiment, the parietal polysaccharides from at least one different yeast species are in an amount of at least 70, 75, 80, 85 or 90 dry weight percent based on the total weight of parietal polysaccharides in the composition. In yet another embodiment, the parietal polysaccharides from at least one different yeast species are in an amount of at least 80, 81, 82, 83, 84, 85, 86, 87, 88, 89 or 90 dry weight percent based on the total weight of parietal polysaccharides in the composition.

In alternative or complimentary embodiments, the parietal polysaccharides from at least one *Candida* species and parietal polysaccharides from at least one different yeast species are in an amount ranging from 1 to 100 weight percent based on the total weight of the composition. In an embodiment, the parietal polysaccharides from at least one *Candida* species and parietal polysaccharides from at least one different yeast species are in an amount ranging from 20 to 80 weight percent based on the total weight of the composition. In another embodiment, the parietal polysaccharides from at least one *Candida* species and parietal polysaccharides from at least one different yeast species are in an amount ranging from 30 to 60 weight percent based on the total weight of the composition. In yet another embodiment, the parietal polysaccharides from at least one *Candida* species and parietal polysaccharides from at least one different yeast species are in an amount of at least 5, 10, 15, 20, 25, 30, 35, 40, 45, 50, 55, 60, 65, 70, 75, 80, 85, 90 or 95 weight percent based on the total weight of the composition. In still a further embodiment, the parietal polysaccharides from at least one *Candida* species and parietal polysaccharides from at least one different yeast species are in an amount of at least 20, 23, 25, 27 30, 33, 35, 37, 40, 43 45, 47 50, 53, 55, 57, 60, 63, 65, 67, 70, 73, 75, 77 or 80 weight percent based on the total weight of the composition. In an embodiment, the parietal polysaccharides from at least one *Candida* species and parietal polysaccharides from at least one different yeast species are in an amount of at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 weight percent based on the total weight of the composition.

In an embodiment, the parietal polysaccharides from at least one *Candida* species are in an amount ranging from 10 to 50 dry weight percent based on the total weight of parietal polysaccharides in the composition; and the parietal polysaccharides from at least one *Candida* species and parietal polysaccharides from at least one different yeast species are in an amount ranging from 30 to 60 weight percent based on the total weight of the composition.

In another embodiment, the parietal polysaccharides from at least one *Candida* species are in an amount of at least 10, 15, 20, 25, 30, 35, 40, 45 or 50 dry weight percent based on the total weight of parietal polysaccharides in the composition; and the parietal polysaccharides from at least one *Candida* species and parietal polysaccharides from at least one different yeast species are in an amount ranging from 30 to 60 weight percent based on the total weight of the composition.

In yet another embodiment, the parietal polysaccharides from at least one *Candida* species are in an amount ranging from 10 to 50 dry weight percent based on the total weight of parietal polysaccharides in the composition; and the parietal polysaccharides from at least one *Candida* species and parietal polysaccharides from at least one different yeast species are in an amount of at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 weight percent based on the total weight of the composition.

In still a further embodiment, the parietal polysaccharides from at least one *Candida* species are in an amount of at least 10, 15, 20, 25, 30, 35, 40, 45 or 50 dry weight percent based on the total weight of parietal polysaccharides in the composition; and the parietal polysaccharides from at least one *Candida* species and parietal polysaccharides from at least one different yeast species are in an amount of at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 weight percent based on the total weight of the composition.

In an embodiment, the at least one *Candida* species is *Candida utilis*. In the present disclosure, it is understood that *Candida utilis* includes both the sexual (*Cyberlindnera jardinii*) and the asexual (*Candida utilis*) forms. In another embodiment, the at least one different yeast species is from *Saccharomyces* sp, *Hanseniaspora* sp, *Hansenula* sp, *Kluyveromyces* sp, *Metschnikowia* sp, *Pichia* sp, *Starmerella* sp and *Torulaspora* sp or mixture thereof. The at least one different yeast species also comprises as well as inter-species hybrids derived from any one of these yeast species. In yet another embodiment, the at least one different yeast species is *Saccharomyces* sp. In still a further embodiment, the at least one different yeast species is *Saccharomyces cerevisiae*. *Saccharomyces cerevisiae* also comprises subspecies such as, but are not limited to *Saccharomyces cerevisiae* var. *boulardii*. In still a further embodiment, the at least one different yeast species is a blend a two or more *Saccharomyces cerevisiae*. In still a further embodiment, the at least one different yeast species is a blend of at least one *Saccharomyces cerevisiae* and at least one *Saccharomyces cerevisiae* var. *boulardii*.

In an embodiment, the composition as defined in the preceding embodiments can be used in modulating and/or stimulating immune responses in animal or human. The term "modulating" when used herein will be understood to refer to any measurable increase or reduction of the immune response. In another embodiment, the composition as defined in the preceding embodiments can be used in improving animal or human health and resistance to infection. In yet another embodiment, the composition as defined in the preceding embodiments can be used in improving animal or human resistance to pathogenic microorganisms. In still another embodiment, the composition as defined in the preceding embodiments can be used in promoting animal breeding performance. In an embodiment, the animal is a domestic animal. Exemplary domestic animal includes, but is not limited to fish, shrimp, calf or piglet.

In an embodiment, the composition as defined in the preceding embodiments can be use in promoting and/or improving intestinal health, intestinal integrity and intestinal morphology of animals. In another embodiment, the composition as defined in the preceding embodiments can be used for stimulating an anti-inflammatory response of animals. In yet another embodiment, the composition as defined in the preceding embodiments can be used for promoting and/or improving growth performance parameters and feed conversion of farmed animals. In still another embodiment, the composition as defined in the preceding embodiments can be used for reducing morbidity and in particular during antibiotic treatments, and mortality of farmed animals. In an embodiment, the composition as defined in the preceding embodiments can be used for reducing mortality of farmed animals. In another embodiment, the composition as defined in the preceding embodiments can be used for reducing diarrhea of animals. In yet another embodiment, the composition as defined in the preceding embodiments can be used for reducing sensitivity to intestinal pathogens. In still another embodiment, the composition as defined in the preceding embodiments can be used for reducing the sensitivity of animals to parasites infestations and related disorders. In an embodiment, the composition as defined in the preceding embodiments can be used for promoting and/or improving the production of skin mucus of aquatic animals or its quality.

In still another embodiment, the composition as defined in the preceding embodiments is useful as an ingredient in conventional animal feeds.

In still another embodiment, the composition as defined in the preceding embodiments is usually presented in formats that are added to a complete animal or human diet or added separately as tablets, pellets, or beads to be consumed directly.

The present disclosure provides a method of modulating and/or stimulating immune responses in animal or human by administering to an animal or a human a composition comprising parietal polysaccharides from at least one *Candida* species and parietal polysaccharides from at least one different yeast species. There is also provided a method of improving animal or human health and/or resistance to infection by administering to an animal or a human a composition comprising parietal polysaccharides from at least one *Candida* species and parietal polysaccharides from at least one different yeast species. There is also provided a method of improving animal or human resistance to pathogenic microorganisms by administering to an animal or a human a composition comprising parietal polysaccharides from at least one *Candida* species and parietal polysaccharides from at least one different yeast species. There is also provided a method of promoting animal breeding performance by administering to an animal or a human a composition comprising parietal polysaccharides from at least one *Candida* species and parietal polysaccharides from at least one different yeast species.

In an embodiment, the combination is in a form of a food additive, a feed additive, a feed material/ingredient, an animal feed or a pharmaceutical product. In another embodiment, the pharmaceutical product can be administered orally or parenterally. In yet another embodiment, the food additive, animal feed can be presented in formats that are added to a complete animal or human diet or added separately as tablets, pellets, or beads to be consumed directly. In still another embodiment, the animal is a domestic animal. Exemplary domestic animal includes, but is not limited to fish, shrimp, calf or piglet.

The following examples serve to further describe and define the invention, and are not intended to limit the invention in any way.

EXAMPLES

Example 1

Dectin 1 is not the only PRR which recognizes yeast parietal polysaccharides. The structure and the architecture of the cell wall are likely to play an important role. We hypothesized here that different yeast species, even with a similar parietal polysaccharides composition, may exhibit different architectures of their parietal polysaccharides network, resulting in the activation of a different set of PRR, not necessarily linked to the activation of Dectin 1. In vitro competition assays as shown in Example 1 using Laminarin, a specific soluble ligand with high affinity for Dectin 1, was done to assess this hypothesis.

In this example, the inventor has made the choice to evaluate the impact of different combinations of parietal polysaccharides extracted from different yeast strains and species on the innate immunity response. The cellular model used in these experiments was primary culture of human monocytes. The capacity of the monocytes to generate oxygen species was evaluated: thanks to chemiluminescence, the production of the anion superoxide was studied. This molecule is issued from the NADPH oxidase, an enzymatic complex encountered at the surface of monocytes. Oxygen species are involved in the killing of living bacteria or fungi phagocytosed by monocytes.

Material & Methods

Cell Culture

Peripheral blood mononuclear cells (PBMC) were obtained from healthy blood donor buffy coats by a standard Ficoll-Hypaque gradient method. Human monocytes were isolated from mononuclear cells by adherence to plastic for 2 hours in SFM medium optimized for macrophages culture, at 37° C. in a humidified atmosphere containing 5% $CO_2$. They were seeded into a multi-well cultured plate and non-adherent cells were removed by washings with HBSS without calcium or magnesium. The remaining adherent cells (>85% monocytes) were incubated in SFM before stimulation.

Assay for Oxygen Species Production

Mononuclear cells were placed in a 96-well microplate. Reactive Oxygen Species (ROS) production was measured by chemiluminescence in the presence of 5-amino-2,3-dihydro-1,4-phthalazinedione (luminol, Sigma) using a thermostatically (37° C.) controlled luminometer (Wallac 1420 Victor2, Finland). The generation of chemiluminescence was monitored continuously for 60 min after incubation of the cells with luminol (66 µM) in basal conditions and in the presence of the different parietal polysaccharides at 100 µg/ml alone or in the presence of graded level of Laminarin (0, 1, 10 and 100 µg/ml depending of the assays). Zymosan was used as a positive control at 100 µg/ml.

Parietal Yeast Polysaccharides Used in this Study:

Parietal polysaccharides extracted from different yeast strains:

Saccharomyces cerevisiae strains: L60, L62, L69, L72
Candida utilis strain: L75 (NRRL-900)

Levels of Parietal polysaccharides tested in the different assays:

Candida utilis strain: the parietal polysaccharide levels were standardized to 30 dry weight percent based on the total weight of the composition.

Saccharomyces cerevisiae strains: the parietal polysaccharide levels were standardized to 30, 35, 45 and 60 dry weight percent based on the total weight of the composition.

Figure 4A:
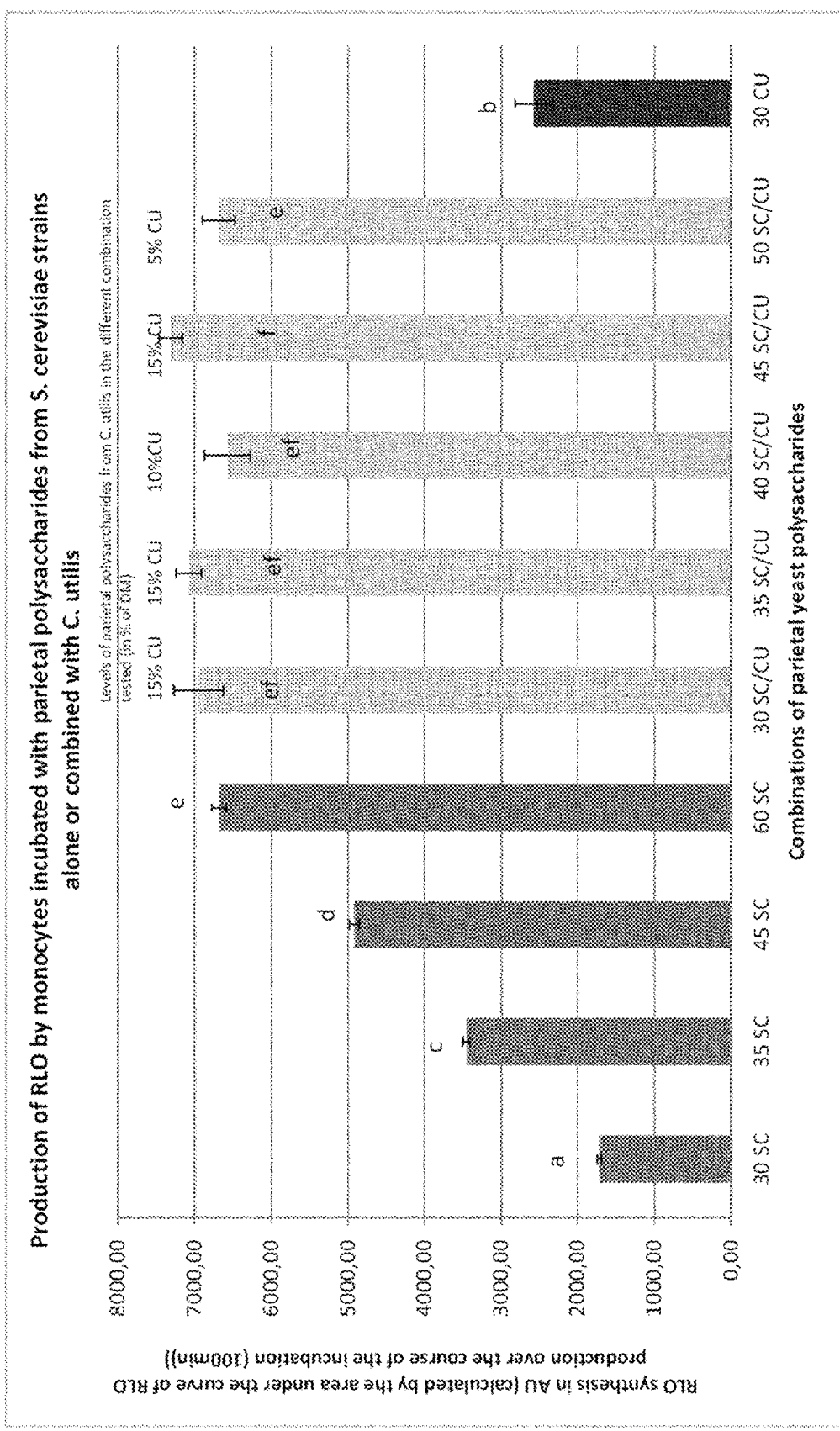
FIGS. 4a and 4b show the In vitro production of ROS by monocytes incubated with different concentrations of parietal polysaccharides from *Saccharomyces cerevisiae* strains alone or combined with parietal polysaccharides from a *Candida utilis* strain (a) whitout Laminarin and (b) with 100 μg of Laminarin, according to example 1, assay 4.
Figure 4:
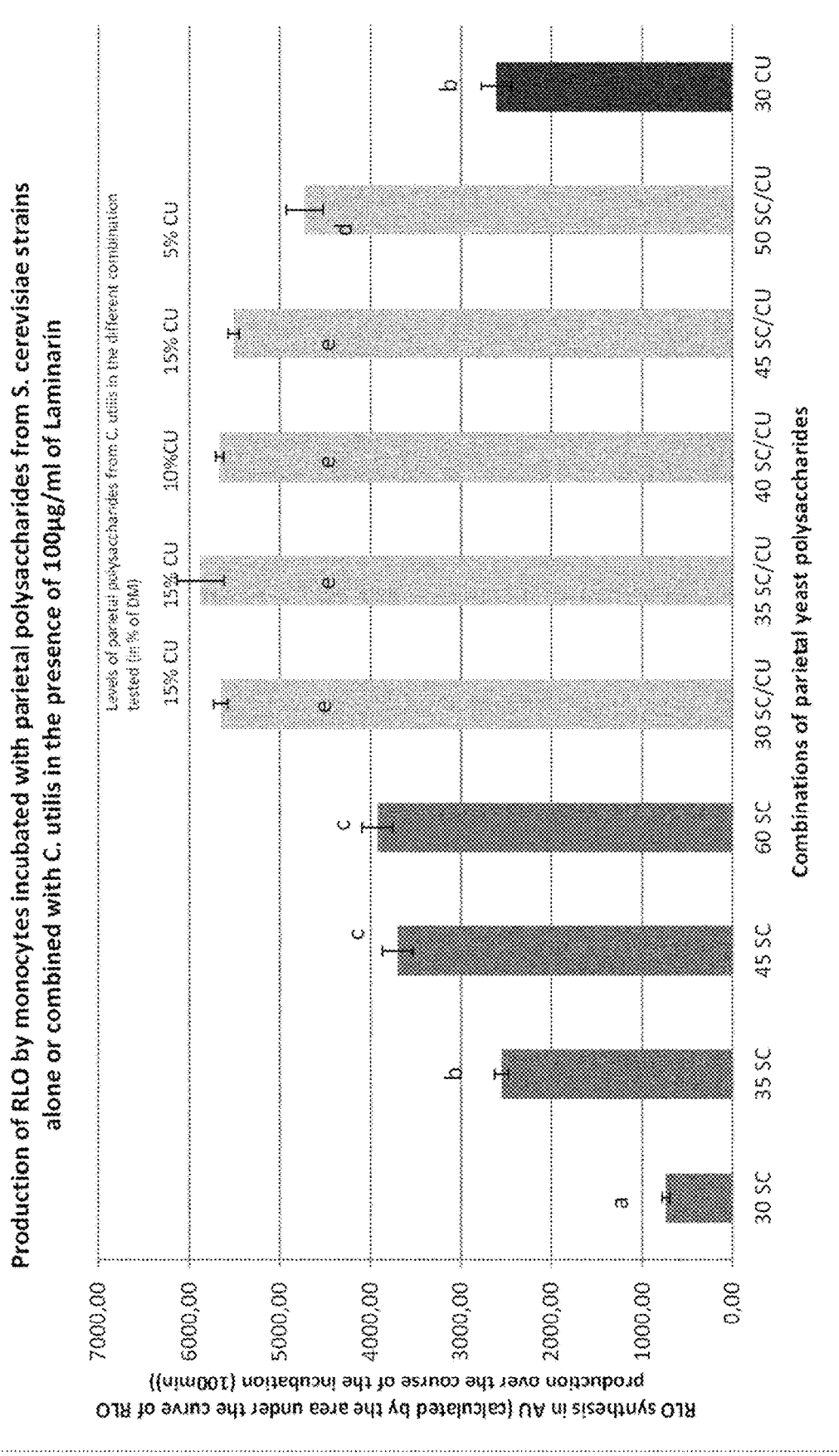

Combination of Candida utilis and Saccharomyces cerevisiae: the polysaccharide levels were standardized to 30, 35, 40, 45 and 50 dry weight percent based on the total weight of the composition. The levels of parietal polysaccharides from Candida utilis in those combinations were respectively 15, 15, 10, 15 and 5 dry weight percent based on the total weight of the composition or 50, 43, 25, 33 and 10 dry weight percent based on the total weight of parietal polysaccharides in the composition (FIGS. 4a,4b)

Results:

Assay 1: In vitro production of ROS by monocytes incubated with parietal polysaccharides from different strains of Saccharomyces cerevisiae with different concentrations of Laminarin. Each parietal polysaccharides fraction from four different strains of Saccharomyces cerevisiae was standardized to 60 dry weight percent based on the total weight of the fraction and tested for their affinity for Dectin 1. As shown in FIG. 1, the parietal polysaccharides from all the strains were able to induce the production of ROS and Laminarin inhibited this induction in a linear dose response manner.

Figure 2:
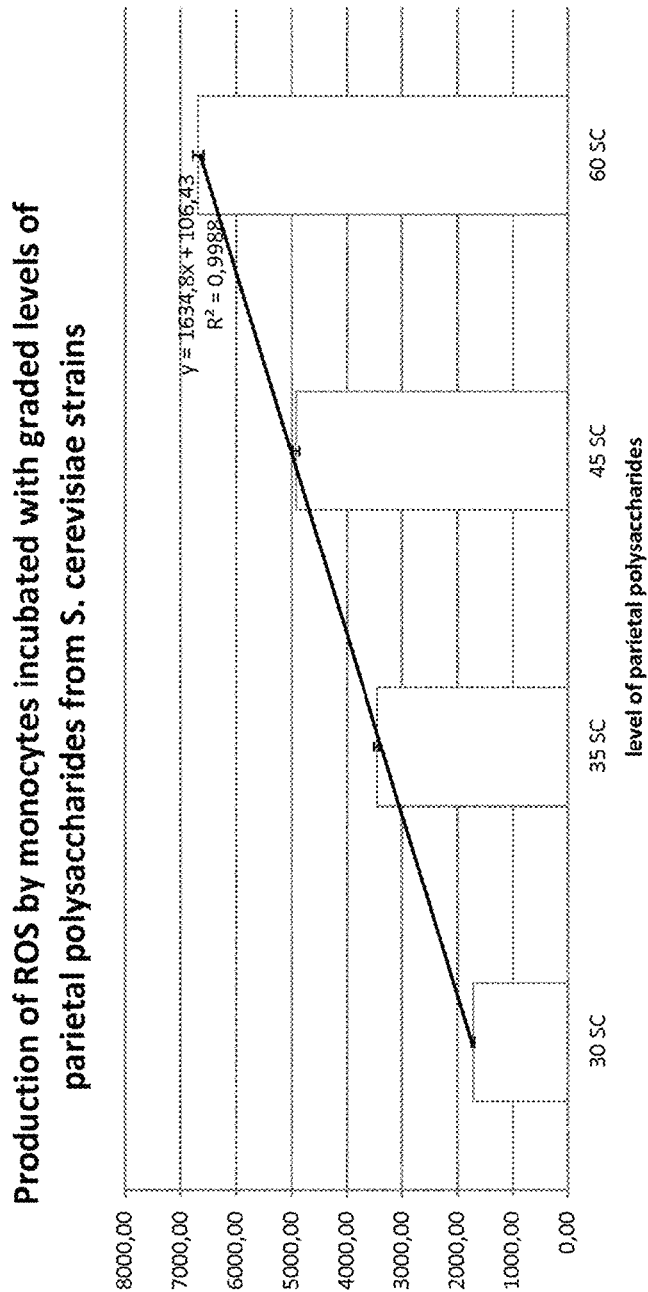
FIG. 2 shows the In vitro production of ROS by monocytes with different concentrations of a blend of parietal polysaccharides from different *Saccharomyces cerevisiae* strains, according to example 1, assay 2.

Assay 2: Dose response of parietal polysaccharides from Saccharomyces cerevisiae on the In vitro production of ROS by monocytes. A blend of parietal polysaccharides from two different Saccharomyces cerevisiae strains (L62 and L69) was prepared and standardized at 30, 35, 45 and 60 dry weight percent based on the total weight of the blend and tested for their induction of the ROS production. As shown in FIG. 2, a linear dose response was obtained over the range of concentrations tested.

Figure 3:
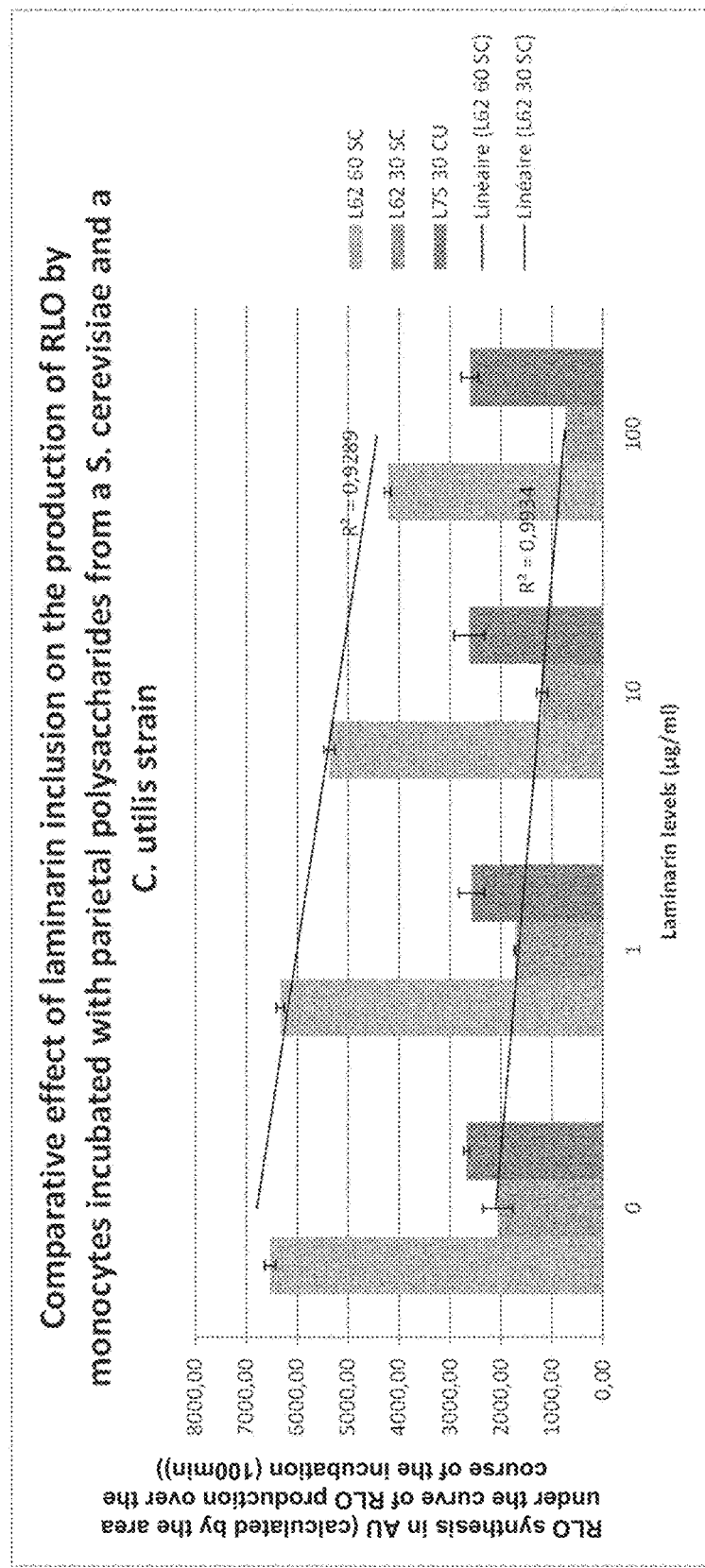
FIG. 3 shows the comparative effect of Laminarin on the In vitro production of ROS by monocytes incubated with parietal polysaccharides from a *Candida utilis* strain or with parietal polysaccharides from a *Saccharomyces cerevisiae* strain, according to example 1, assay 3.

Assay 3: Comparative effect of laminatin on the in vitro production of ROS by monocytes incubated with parietal polysaccharides from a Candida utilis strain or with parietal polysaccharides from a Saccharomyces cerevisiae. The parietal polysaccharides fraction from a proprietary strain of Candida utilis were standardized to 30 dry weight percent based on the total weight of the fraction and tested for its affinity for Dectin 1. Similarly, the parietal polysaccharides fraction from a strain of Saccharomyces cerevisiae (L62) was standardized respectively to 30 and 60 dry weight percent based on the total weight of the fraction and tested for their affinity for Dectin 1. As shown in FIG. 3, in absence of Laminarin, the parietal polysaccharides fraction of Candida utilis and the parietal polysaccharides fractions of Saccharomyces cerevisiae were able to induce the production of ROS. In FIG. 3, an increase in the concentration of Laminarin increases the inhibition of the production of ROS by the parietal polysaccharides fractions of Saccharomyces cerevisiae. However, an increase in the concentration of Laminarin showed no inhibition of the production of ROS by the parietal polysaccharides fraction of Candida utilis, even at 100 µg/ml.

Assay 4: In vitro production of ROS by monocytes incubated with different concentrations of parietal polysaccharides from Saccharomyces cerevisiae strains alone or combined with parietal polysaccharides from a Candida utilis strain (a) without Laminarin and (b) with 100 µg of Laminarin;

As shown in FIGS. 4a and 4b, the presence of parietal polysaccharides from Candida utilis in the different compositions leads to an enhancement of the production of ROS by monocytes even at low inclusion rate (i.e. 5 dry weight percent based on the total weight of the composition). As shown in FIG. 4b, the compositions comprising parietal polysaccharides from Candida utilis and parietal polysaccharides from at least one Saccharomyces cerevisiae were not affected by the inhibiting effect of Laminarin over the polysaccharides from Saccharomyces cerevisiae alone (as shown in FIGS. 1 and 3), even at the lower inclusion rate (i.e. 5 dry weight percent based on the total weight of the composition or 10 dry weight percent based on the total weight of parietal polysaccharides in the composition).

Example 2

A composition comprising parietal polysaccharides from a Candida utilis (CU) and parietal polysaccharides from a Saccharomyces cerevisiae (SC) was tested as a preventive feeding strategy to mitigate penaed shrimps sensitivity to vibriosis. The parietal polysaccharides were in an amount of 50 weight percent based on the total weight of the composition (50 SC/CU).

With the aim to assess the benefit of 50 SC/CU parietal polysaccharides vs SC parietal polysaccharides alone, we applied an In vivo disease challenge on penaeid shrimp juveniles. The infection method was immersion and we use a virulent Vibrio parahaemolyticus able to induce the acute hepatopancreatic necrosis syndrome.

The tested parietal polysaccharides were:
  50 SC/CU parietal polysaccharides containing 6 dry weight percent of parietal polysaccharide from Candida utilis NRRL-900 (based on the total weight of the composition, or 12 dry weight percent based on the total weight of parietal polysaccharides in the composition): 3 doses were tested: 0.04%; 0.08%, and 0.12% in feed
  60 SC parietal polysaccharides from one strain of S. cerevisiae (CNCM I 1079) tested at 0.12% in feed The trials were performed with Litopenaeus vannamei juvenile of 2.07±0.05 g that were fed for 21 days with diets supplemented or not with the tested Candidates prior to an immersion challenge with 100 ml of a culture of a virulent V. parahaemolyticus strain able to induce AHPNS at $1.1 \times 10^9$ CFU/ml (grown in TSB+2% NaCl (TSB+) at 28° C. for 18 h). The mortalities were monitored over 10 days and the cumulative survival for each diet was statistically compared to the control within each trial. Kaplan and Meier survival curves (Kaplan and Meier, 1958) were also constructed for each diet and the curves were compared using the log-rank test to determine differences between curves and whether the trends in survival were different between curves. The significance level was set at P=0.05.

The 50 SC/CU treatment showed a linear dose response to reduce the mortality induced by the pathogenic strain (Log Rank (Mantel-Cox), p<0.01). The survival was yet significantly improved at 0.04% inclusion rate compared to the positive control (infected). The 60 SC/CU only showed a marginal improvement at 0.12%.

Protocol:

Juvenile *Penaeus vannamei*, were fed with a commercially prepared shrimp diet which was mixed with the tested products for 21 days prior to bath exposure to *Vibrio parahaemolyticus* (agent causing acute hepatopancreatic necrosis disease—AHPND) to determine if the feed additive will have effects on survival and infection rates.

Aquaria and Experimental Design:

The SPF (specific pathogen free) animals utilized in this example have been checked for important infectious disease including WSSV (White Spot Syndrome Virus), TSV (Taura Syndrome Virus, IMNV (Infectious Mionecrosis Virus), AHPND (Acute Hepatopancreatic Necrosis Disease using both histopathology and PCR techniques. 12 days old post-larvae were transferred from hatchery to a wet lab and were grown in strict biosecurity for another 45 days to reach the size of 1-2 gram. One day prior to the start of the study, SPF *P. vannamei* at 1-2 gram/each were transferred to 27 90 L tanks (35 shrimps/tank). All shrimp in each tank were weighed in-group prior to stocking for growth rate calculation at termination of the trial. All animals in these tanks were fed their respective test diet for 21 days (Table 1).

Four replicate tanks per treatment were fed the prepared feed containing the tested products. Four tanks were designated as positive controls and four other tanks served as negative controls. The negative control tanks were also be fed with a commercially pelleted shrimp diet but were not be challenged with the EMS/AHPND causing *Vibrio parahaemolyticus*. All tanks received their respective diet at approximately 5% bodyweight each day.

Sixteen treatment tanks were challenged with *Vibrio parahaemolyticus* after 21 days of the feed containing Feed additive administration. Meanwhile, positive control tanks were fed with the same commercial shrimp diet without any addition and were challenged with *Vibrio parahaemolyticus* on day 21 of the trial. Challenge shrimp were kept for another 10 days for survival recording and growth rate monitoring.

Challenge Methods:

In this study, the shrimps were subjected to an immersion challenge. Tryptic Soy Broth +2% (TSB+) sodium chloride inoculated with a consistently virulent strain of *Vibrio parahaemolyticus*, incubated for 18 hours, was added directly into tanks. The bacterial suspension was added into tank to achieve the bacterial density measured by optical density absorbance (OD600 nm). During challenge period, shrimp were kept on their respective dietary treatment for another 10 days.

Results

Figure 5:
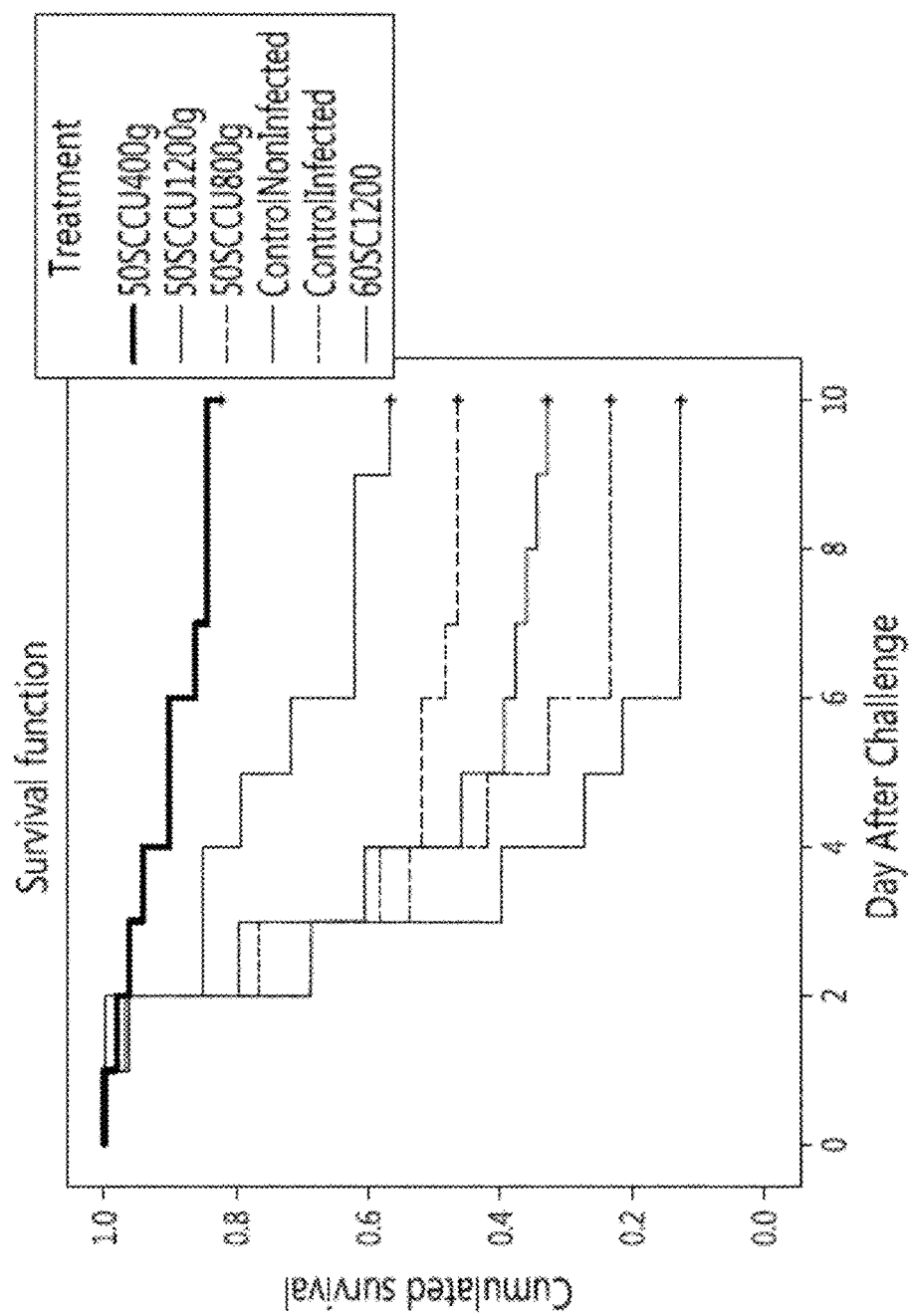
FIG. 5 shows the survival rate function of penaed shrimp infected with *Vibrio parahaemolyticus* and treated with different compositions of parietal polysaccharides in accordance with the Kaplan Meyer statistical procedure according to example 2.

Final survival rates at the end of the trial after statistical treatment are reported in Table 1. The FIG. 5 reports the distributions of the survival rate during the course of the experiment for the different group of shrimps according the Kaplan Meyer procedure.

TABLE 1

Final survival rate: Summary of the treatment of the observations

| Treatment | N total | Number of events | Censuré N | Percentage |
|---|---|---|---|---|
| 50SCCU400g | 61 | 41 | 20 | 32.8% |
| 50SCCU1200g | 53 | 23 | 30 | 56.6% |
| 50SCCU800g | 54 | 29 | 25 | 46.3% |
| ControlNonInfected | 51 | 9 | 42 | 82.4% |
| ControlInfected | 55 | 48 | 7 | 12.7% |
| 60SC1200 | 43 | 33 | 10 | 23.3% |
| Global | 317 | 183 | 134 | 42.3% |

Tables 2 and 3 show the statistical differences between the survival distributions from the different groups of shrimps.

As shown in Table 2, all the tests applied revealed a highly significant treatment effects between the survivals distributions.

TABLE 2

Statistical comparison: Test for equality of survival distributions for different levels of Treatments.

| | Khi-deux | ddl | Sig. |
|---|---|---|---|
| Log Rank (Mantel-Cox) | 66.168 | 5 | 0.000 |
| Breslow (Generalized Wilcoxon) | 58.851 | 5 | 0.000 |
| Tarone-Ware | 63.183 | 5 | 0.000 |

As shown in Table 3, the bacteria challenge significantly affects the survival of the shrimp in all the groups when the kinetics of mortality for each infected group were compared to the negative control (non-infected group) using the Kaplan-Meier method and the Log Rank (Mantel-Cox) test. Besides, these In vivo results confirm the beneficial effect of the composition comprising parietal polysaccharides from *Saccharomyces cerevisiae* and *Candida utilis* in modulating and/or stimulating the natural defenses and improve animal performance under challenging conditions (Table 3).

TABLE 3

Statistical comparison of the distribution using the Log Rank (Mantel-Cox) test: Test for equality of survival distributions between the different treatments.

| | | 50SCCU400g | | 50SCCU1200g | | 50SCCU800g | | 60SC1200 | |
|---|---|---|---|---|---|---|---|---|---|
| | Treatment | Khi-deux | Sig. | Khi-deux | Sig. | Khi-deux | Sig | Khi-deux | Sig |
| Log Rank (Mantel-Cox) | 50SCCU400g | | | 8.521 | 0.004 | 1.803 | 0.179 | 0.515 | 0.473 |
| | 50SCCU1200g | 8.521 | 0.004 | | | 1.804 | 0.179 | 13.679 | 0.000 |
| | 50SCCU800g | 1.803 | 0.179 | 1.804 | 0.179 | | | 3.626 | 0.057 |
| | Control Non-Infected | 29.106 | 0.000 | 8.047 | 0.005 | 15.782 | 0.000 | 37.527 | 0.000 |

TABLE 3-continued

Statistical comparison of the distribution using the Log Rank (Mantel-Cox) test: Test for equality of survival distributions between the different treatments.

| Treatment | 50SCCU400g | | 50SCCU1200g | | 50SCCU800g | | 60SC1200 | |
|---|---|---|---|---|---|---|---|---|
| | Khi-deux | Sig. | Khi-deux | Sig. | Khi-deux | Sig | Khi-deux | Sig |
| Control Infected | 4.526 | 0.033 | 27.823 | 0.000 | 10.448 | 0.001 | 1.908 | 0.167 |
| 60SC1200 | 0.515 | 0.473 | 13.679 | 0.000 | 3.626 | 0.057 | | |

Example 3

The results of the present example in seabass showed a positive effect of «50 SC/CU parietal polysaccharides» vs «60 SC parietal polysaccharides» on fish performance and response to stress.

Dicentrarchus labrax with an average weight of 15.4 g were subjected to a ten week feeding trial with 0.08% of «50 SC/CU parietal polysaccharides» vs 0.2% of «60 SC parietal polysaccharides».

Feed was formulated to contain high levels of Soybean meal (40%) as shown in Table 4.

TABLE 4

Diet formulation

| Basal ingredients | Control | 60 SC parietal polysaccharides | 50 SC/CU parietal polysaccharides |
|---|---|---|---|
| Soybean meal | 38.93 | 38.93 | 38.93 |
| Corn Starch | 16.63 | 16.63 | 16.63 |
| Glutalys | 16 | 16 | 16 |
| Herring meal LT94 | 15 | 15 | 15 |
| Fish oil | 11.94 | 11.94 | 11.94 |
| PNP VitaMin premix | 1 | 1 | 1 |
| CMC-binder | 0.5 | 0.5 | 0.7 |
| tested products | | 0.2 | 0.08 |

3 tanks of 25 fishes per treatment. Salinity stress applied at week 8. Parameters recorded: growth performance/intestinal morphology/intestinal microflora.

Table 5 shows the final performance at week 10.

TABLE 5 performance at week 10

| Parameters | Control | 50 SC/CU | 60 SC | P-value |
|---|---|---|---|---|
| Initial body weight (g/fish) | 15.47 ± 0.20a | 15.44 ± 0.21a | 15.45 ± 0.19a | |
| Final body weight (g/fish) | 33.92 ± 0.91a | 37.08 ± 1.19b | 36.11 ± 0.63b | 0.05 |
| SGR | 1.25 ± 0.03a | 1.39 ± 0.03b | 1.35 ± 0.04b | 0.039 |
| Feed conversion ratio (g/g) | 1.66 ± 0.02a | 1.45 ± 0.04c | 1.51 ± 0.02b | 0.027 |
| Survival (%) | 93.33 ± 2.31a | 100.00 ± 0b | 97.33 ± 4.62ab | 0.09 |

All data are presented as means±standard deviation (SD). Data were transformed where necessary and statistical analysis was conducted using SPSS statistics version 18 for windows (SPSS Inc., Chicago, Ill., USA) and significance was accepted at the P<0.05 level. All Data were analysed using a one-way ANOVA. Significant differences between control and experimental groups were determined using the non-parametric test of Mann-Whitney.

Figure 6A:
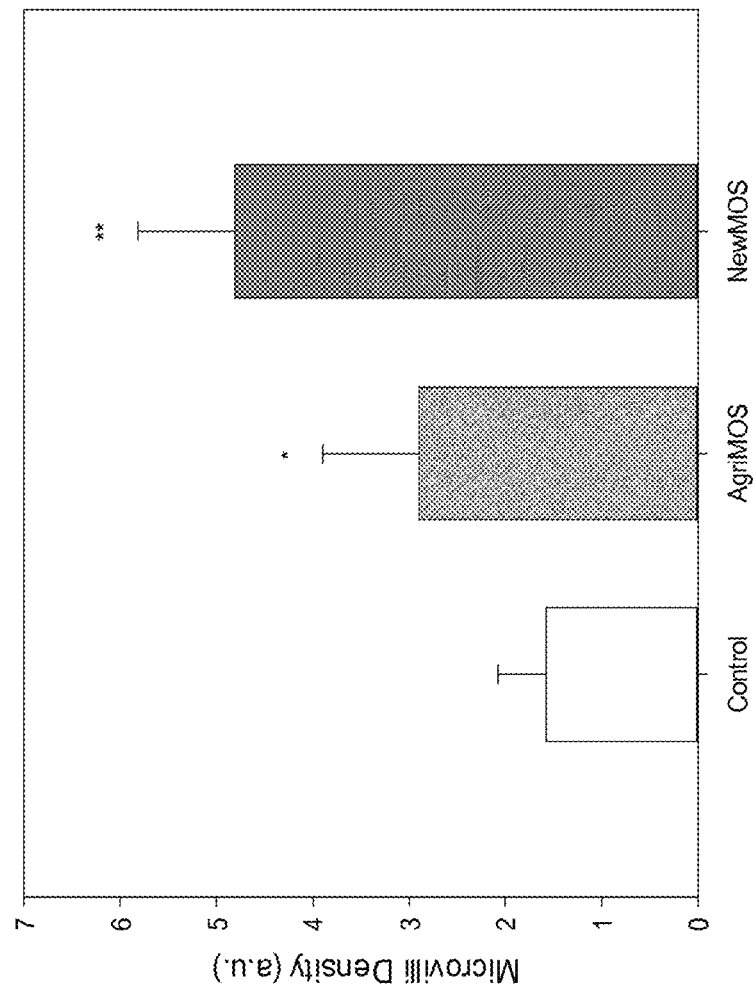
FIGS. 6a and 6b show the microvilli density of sea bass distal intestine by electron microscopy after feeding on experimental diets in accordance with the present disclosure at week 5 and 10 according to example 3.
Figure 6B:
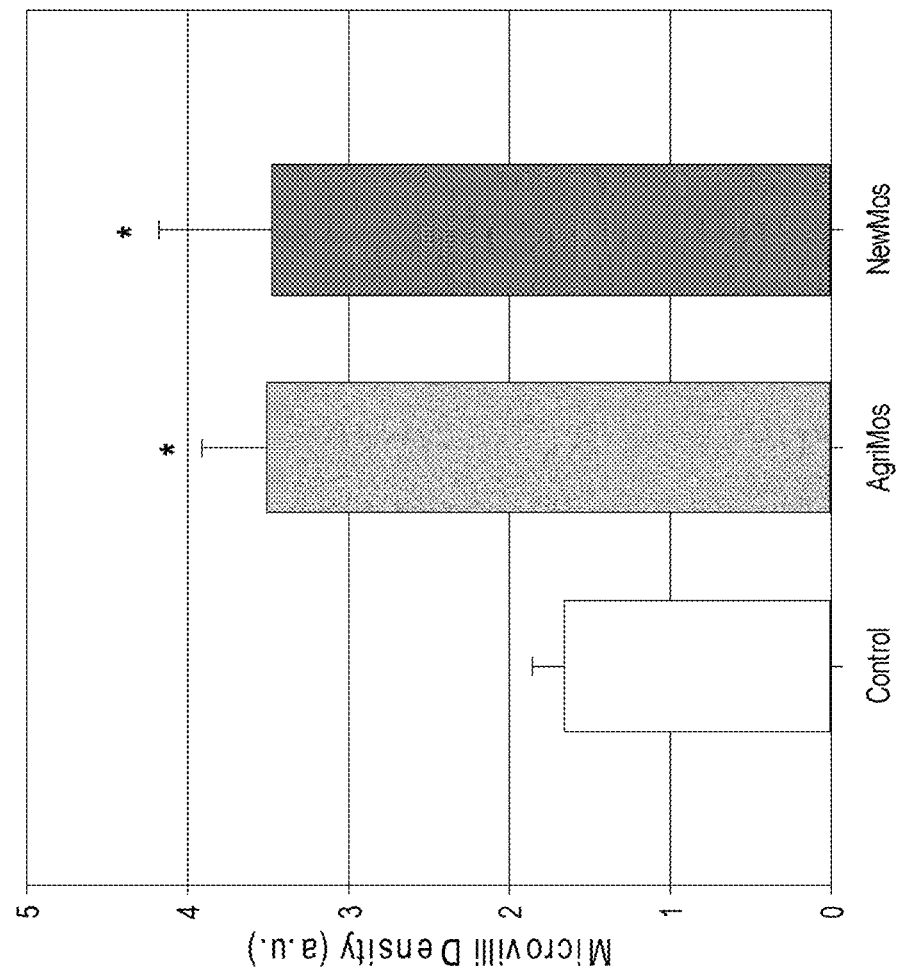

FIGS. 6a and 6b show the scanning electron microscopy results of the microvilli density of sea bass distal intestine after feeding on experimental diets at respectively week 5 and 10. Data expressed as means±S.D (n=3). Significant differences from corresponding control are indicated (*) P<0.01, and (**) P<0.001. Data was transformed where necessary and statistical analysis was conducted using SPSS statistics version 18 for windows (SPSS Inc., Chicago, Ill., USA) and accepted at the P<0.05 level. A one-way ANOVA was used to analyse data and significant differences between the control and experimental groups were determined using Tukey's post hoc test.

TABLE 6

| | Control | 50 SC/CU parietal | 60 SC parietal polysaccharides | P-value |
|---|---|---|---|---|
| Perimeter ration (week 5) | 3.0 ± 0.4a | 3.6 ± 0.4b | 3.2 ± 0.4ab | <0.05 |
| Perimeter ratio (week 10) | 3.2 ± 0.0a | 4.3 ± 0.3b | 4.1 ± 0.4ab | <0.02 |
| Fold length (week 5) | 324.6 ± 06.5 | 383.6 ± 146.6 | 334.8 ± 98.7 | n.s |
| Fold length (week 10) | 318.0 ± 74.6a | 391.3 ± 77.0b | 336.9 ± 96.0ab | <0.02 |

Light microscopy at week 5 and 10

All data are presented in Table 6 as means±standard deviation (SD). Data were transformed where necessary and statistical analysis was conducted using SPSS statistics version 18 for windows (SPSS Inc., Chicago, Ill., USA) and significance was accepted at the P<0.05 level. All Data were analysed using a one-way ANOVA. Significant differences between control and experimental groups were determined using post hoc Tukeys HSD test.

Figure 7:
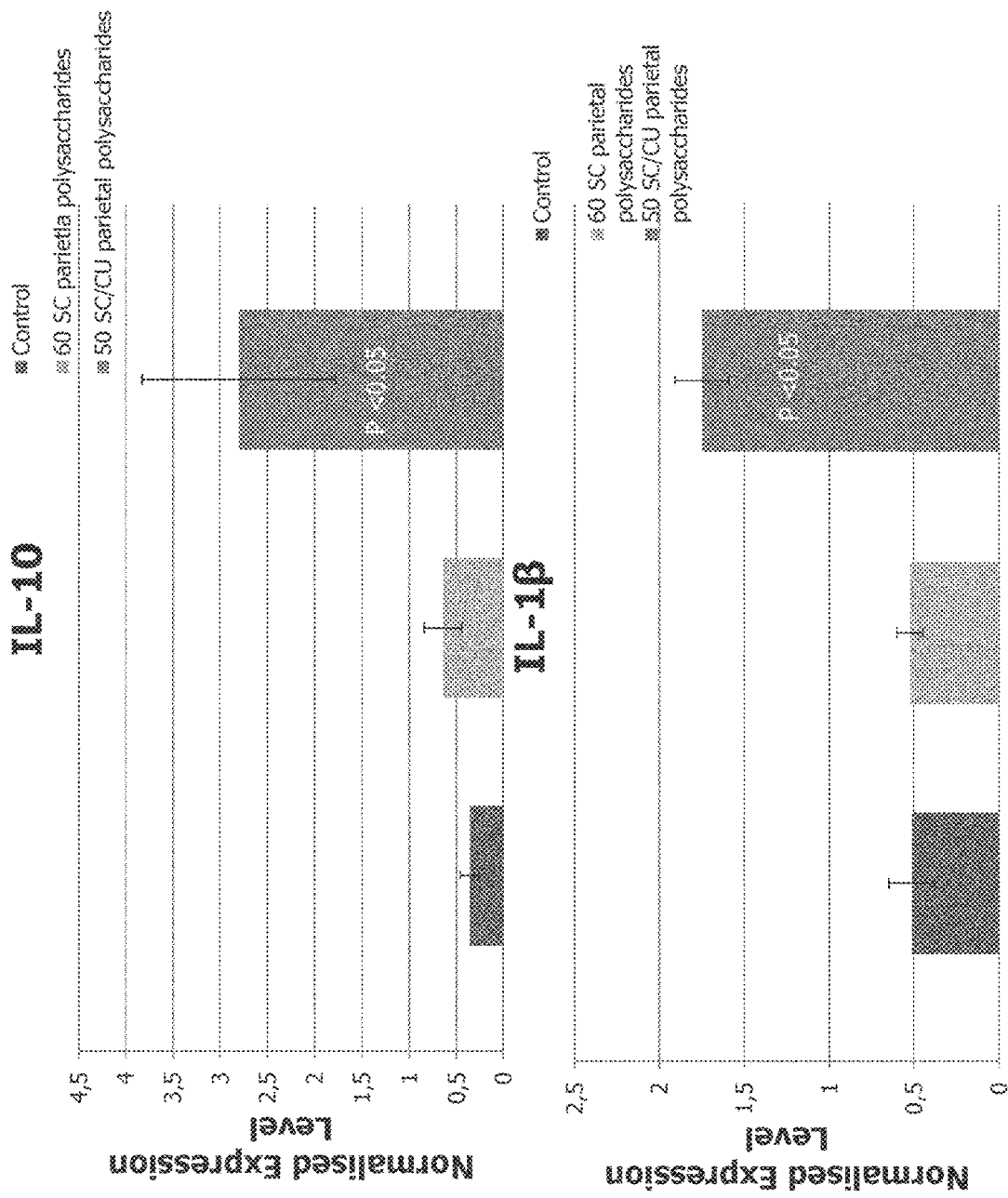
FIG. 7 shows the expression of two immune genes (IL 1β and IL10) in the distal intestine after feeding on experimental diets in accordance with the present disclosure at week 10 according to example 3.

FIG. 7 shows the expression of two immune genes (IL1β and IL10) in the distal intestine of sea bass after feeding on experimental diets in accordance with the present disclosure at week 10.

Example 4

This example demonstrates the effect of supplementing weaned piglets with combination of parietal polysaccharides in accordance with the present disclosure in the 2$^{nd}$ phase feed.

Trial Set Up

Duration of the trial: 42 days

Animals material and husbandry conditions:

Weaned Piglets were housed in pens of 12 piglets. In one building, 6 pens were allocated to one of the two treatments (Control and Treatment). Two series of trial were repeated over time resulting in 12 replicate pens per treatment when analyzing the 2 series together.

Test product: 50 SC/CU parietal polysaccharides with 6% CU

Treatments: The trial consisted of 2 treatments:
T-1—control—normal diets, without yeast derivatives
T-2—control diet supplemented with 50 SC/CU parietal polysaccharides at 0.08%
Diets Animals were fed a two phase meal diets as shown in Table 7.

TABLE 7 two phase meal diets

| | Phase | |
|---|---|---|
| | P1 | P2 |
| Weight start, kg | 7.63 ± 1.14 | 11.23 ± 1.37 |
| Duration, days | 12 days | 30 days |

Measured zootechnical parameters:
Body weight per pen at start and at the end of each feeding phase,
Feed consumption per pen for the 2$^{nd}$ feeding phase
Mortality and culling rate
Statistical Analysis
Results are analysed with GLM (Generalized Linear Model) univariate model, using SPSS.
Results:
A. Growth Performance
As shown in Table 8, significant effects were detected on the final body weight and the average daily gain. This effect is mainly explained by significant better performance during the second phase with significant higher daily growth rate and feed conversion ratio in the treated group.

TABLE 8

| Diet | WeightPeltWeaning | WeightPelt1age | WeightPelt2age | ConsoPelt1age | GMQ1age | GMQ2age | GMQPS | IC2age |
|---|---|---|---|---|---|---|---|---|
| T2 | | | | | | | | |
| Average | 7.3208 | 10.5867 | 26.9967 | 25.3850 | 0.2542 | 0.5975 | 0.4867 | 1.5442 |
| N | 12 | 12 | 12 | 12 | 12 | 12 | 12 | 12 |
| SD | 1.50841 | 1.78012 | 3.43864 | 3.89799 | 0.07090 | 0.06210 | 0.05449 | 0.09558 |
| T1 | | | | | | | | |
| Average | 7.5292 | 11.0717 | 23.3625 | 22.3625 | 0.2750 | 0.4467 | 0.3908 | 1.8333 |
| N | 12 | 12 | 12 | 12 | 12 | 12 | 12 | 12 |
| SD | 0.99859 | 1.54490 | 3.94419 | 4.60637 | 0.06974 | 0.08283 | 0.07821 | 0.16621 |
| P | 0.694 | 0.483 | 0.025 | 0.097 | 0.476 | <0.001 | 0.002 | <0.001 |

Other observations: Only one piglet died in one of the treated pen vs three (3) in the control pens, all mortalities were due to meningitis. Less ear biting observed in Treatment group. Stool more liquid in Control group.

Example 5

This example assesses the effect of a 50 SC/CU parietal polysaccharides composition when supplemented through the solid feed on the zootechnical and health performances of calves before and after weaning Duration of the study: 6 weeks.
Materials and Methods
Animals involved:
Total animals: 129 animals at beginning, 125 at the end.
Sex: Male
Breed: Friesian (origin: different farms from France)
Experimental Treatments Two dietary treatments were compared, using the same meal flour supplemented with different products:
As T0: Control diet without any product.
T1: same diet supplemented with a 50 SC/CU parietal polysaccharides
2 first weeks: 5 g/animal/day=2.7 g/kg starter feed
then: 3 g/animal/day=1.6 g/kg starter feed.

Experimental Design

Upon arrival in the farm, animals were randomly allocated to the pens. Six days later, the trial began and animals were weighed and pens homogenised by average body weight and average standard deviation of body weights. All pens were conducted contemporaneously. Start weight was 53.9±4.3 kg on average, whereas the average age at start was 27.3±4.4 days.

Site Description and Feeding

All animals were housed in the same building, in straw-bedded pens of 10-11 animals. Four pens per treatment were involved: three pens of 11 animals and one pen of 10 animals each=43 animals per treatment. Every pen had a feeder without any contact between feeders from one pen to another. Straw was shared between two pens, but without cross contamination between treatments. Milk was distributed individually twice a day at 8:00 AM and 6:00 PM. Calf concentrate was manually distributed once a day in feeding troughs, and quantity distributed was weighed each day before distribution. All animals had free access to straw.

Animals were fed according to the following schedule:
Ds Arrival—2 weeks: 2×1.5 L/day of a colostrum milk dilution (25% CP and 19.5% fat) and then milk replacer (22% CP and 18% fat)+solid feed (flour meal) ad lib+straw ad lib+water ad lib
2 weeks—weaning (34 d): 1×2 L/day of Milk replacer (19% CP and 15% fat)+solid feed (flour meal) ad lib+straw ad lib+water ad lib
Weaning—Departure: solid feed (flour meal) ad lib+straw ad lib+water ad lib Weaning was done when calves showed good body condition and began to eat more than 1 kg/day/animal.

Parameters Recorded and Methods Applied

Individual live weights: Calves were weighed individually every two weeks from the beginning until the end of the study at 10:00 AM (total of 4 weights). Feed consumption: Feed consumption (concentrate) was recorded on a pen basis weekly=summary of weighed feed offered every day-weighed refusal the last day of the week.

Results
Body Weight (BW) and Average Daily Gain (ADG)

As shown in Table 9, the average body weight (BW) of animals fed with T1 tended to be better than animals fed with T0. No interaction between treatment and period was found. Initial and final BW (BW0 and BW42 resp.) were numerically higher for T1.

TABLE 9

Body Weights during the trial

|  | T0 | T1 |
|---|---|---|
| Age 0, d | 28.4 | 27.7 |
| Average BW, kg | 74.2 | 75.8* |
| BW 0, kg | 53.6 | 54.4 |
| BW 14, kg | 62.8 | 63.9 |
| BW 27, kg | 71.9 | 73.3 |
| BW 42, kg | 87.9 | 89.9 |

As shown in Table 10, the average Daily gains were not different between treatments, although animals from T1 had a numerically better gain than those from T0.

TABLE 10

Average Daily gains during the trial

|  | T0 | T1 |
|---|---|---|
| ADG, kg/d | 0.79 | 0.83 |
| ADG 14, kg/d | 0.6 | 0.65 |
| ADG 27, kg/d | 0.71 | 0.71 |
| ADG 42, kg/d | 1.07 | 1.12 |
| ADG total, kg/d | 0.8 | 0.84 |

Standard Deviations within the pen give a good indication of heterogeneity of weights and gains, when farmers are looking for better homogeneity as a consequence of more even intakes. Standard deviations of T1 are significantly lower than T0, meaning than Control animals have greater heterogeneity of body weights than treated animals (Table 11). Looking at heterogeneity of growth, no statistical significance was observed but numerically, Control animals have more heterogeneous growth than treated-group animals.

TABLE 11

Standard Deviations of BW and ADG (within the pens) during the trial

|  | T0 | T1 |
|---|---|---|
| SD BW, kg | 9.63a | 7.29b |
| SD ADG, kg/d | 0.299 | 0.219 |

Concentrate Intake and Feed Efficiency (FE) and Feed Conversion Ratio (FCR)

Statistical analysis of total concentrate intake (sum of intake on total period/number of animals by pen) by week did not show any difference. Feed Conversion ratio analysis did not show any significant difference between the treatments.

Diarrhoeas and Morbidity

As shown in Table 12, the animals from T1 showed a lower number of days on diarrhoeas and a lower number of antibiotic treatments compared to the control T0.

TABLE 12

Number of days on Diarrhoea and number of antibiotic treatments

|  | T0 | T1 |
| --- | --- | --- |
| Number of antibiotic treatments/animal | 1.63 | 0.93 |
| Number of days on diarrhoea/animal | 0.44 | 0.12 |

A Mann Whitney test applied on the percentage of animals treated at least once for diarrhoea showed a significant reduction in T1 compared to T0, and a trend of reduction for the percentage of animals treated at least once with antibiotics.

Percentage of animals treated at least once with antibiotics and for diarrhoea.

|  | T0 | T1 |
| --- | --- | --- |
| % animals treated at least once with antibiotics | 53.5 | 32.6T |
| % animals treated at least once for diarrhoea | 23.3 | 6.9* |

Example 6

Juveniles of *Penaeus vannamei* were fed with commercially prepared shrimp diets which were mixed with a feed additive product provided by LALLEMAND for 14 days prior to a 14 days challenge with *Enterocytozoon hepatopenaei*, a microsporidian parasite, to determine if any dosage of the feed additives have positive effects on survival rate, reduces infection rate and parasite load.

Materials & Methods

SPF (specific pathogen free) shrimp juveniles were utilized in this study. Those shrimp were checked for important infectious diseases including WSSV (White Spot Syndrom Virus), TSV (Taura Syndrom Virus), IMNV (Infectious Myonecrosis Virus), EMS/AHPND (early mortality syndrome/acute hepatopancreatic necrosis syndrome) and EHP (*Enterocytozoon hepatopenaei*). One day prior to the start of the study, SPF *Penaeus vannamei* at 1.50±0.09 gram per each were transferred to 120 L tanks (with 30 shrimp.tank[1]) containing 90 L of water at salinity of 20 ppt. Each tank was out-fitted with a submerged biological filter containing activated coral.

Experimental Design

The experiment was set up as a completely randomized design in which, every treatment was randomly designed with the different tanks. Total length of the trial: 29 days, including 1 day of acclimation, 14 days of feed additive administration, followed by 14 days EHP challenge under the same feeding treatments according to table 13. Shrimp in all tanks received their respective diets at satiation four times per day during the trial (Table 14). Five tanks were fed with the prepared feed containing the Feed additive Five tanks were designated as positive controls for a co-habitation challenge and five tanks served as negative controls.

TABLE 13

Timing of the experiment

| Timing | Day 0 | Day 1 | Day 14 | Day 15 | Day 17 | Day 18 | Day 27 | Day 28 |
| --- | --- | --- | --- | --- | --- | --- | --- | --- |
| Feeding | Acclimation | PRE-CHALLENGE | X | | POST-CHALLENGE | | | |
| Challenge | | | | | | | | |
| Weight shrimp | | X | | | | | | X |
| qPCR test for EHP | | X | | X | X | | X | |

TABLE 14

Definition of all 120 L aquaria utilized in the EHP study

| No. | Treatment | Feed | Challenge method |
| --- | --- | --- | --- |
| 1 | Negative control (F) | Com diet | Co-habitation (+SPF shrimp) |
| 2 | Positive control (G) | Com diet | Co-habitation |
| 3 | 50 SC/CU parietal polysaccharides | Com diet + product A (800 g/ ton feed) | Co-habitation |

Shrimp Diets Manufacturing

The feed additives were mixed with the feed meal and added with binder (CMC—carboxythylcellulose) and moisture before being extruded by a pressurized meat grinder. The feed was then dried at 50 degree Celsius for 6 hours. The feed were crushed to the expected size (1.5-2 mm in length) used for the study.

Challenge Method

A standardized co-habitation challenge method was used to challenge small juvenile shrimp with the *Enterocytozoon hepatopenaei* that causes EHP—a microsporidian parasite disease simulating the natural routes of infection.

The SPF and affected shrimps were separated by a net divider that allows for free exchange of water. The co-habitation challenge method is designed as follow: in each 120 liters plastic tank, a 50 cubic liters rectangular net is fitted. During the challenge, 20 EHP-infected shrimp were stocked inside the suspended net, and 30 SPF shrimp were stocked outside. Both EHP-infected shrimp and SPF shrimp were fed with the test diets of each respective treatment for another 14 days. Negative control (F) was also treated with the same challenge method. However, the 20 SPF shrimp instead of 20 EHP-affected shrimp were stock inside the suspended net. During the challenge period, both shrimp inside the net and shrimp outside the net of negative control were fed with a commercial shrimp diet.

The parasite load density of EHP-affected shrimp was 5.05E+06 CFU/g of *Enterocytozoon hepatopenaei* at the start of the challenge.

Sampling and Observation

Testing by qPCR for EHP was done on 5 shrimp/tank/time-point at 3 time-points: day 14 (right before challenge) to confirm the EHP-free status of the SPF shrimp, day 15 (24 hours after challenge), and day 18 (96 hours after challenge) to quantify for the parasite load. At termination of the challenge study, all live animals were counted as survivors.

Statistical Analysis

The comparison of the means from seven treatments was made with ANOVA using a Fisher's LSD test and the significant differences were considered when $P<0.05$.

Results

Shrimp Performance Parameters

The mean production parameters over 28 days of the experimental period are given in table 15. Values represent the means of five replicates.

TABLE 15

| | Initial weight (g) | Final weight (g) | Total amount of feed (g) |
|---|---|---|---|
| Treatment A | 1.51 ± 0.10 | 3.74 ± 0.61 | 72.05 ± 6.87 |
| Treatment F | 1.54 ± 0.12 | 3.54 ± 0.60 | 63.89 ± 5.70 |
| Treatment G | 1.55 ± 0.10 | 3.91 ± 0.66 | 48.68 5.52 |
| | | | 48.69 |

Challenge Trial Surviving Rates

Survival rates of the treatments after 14 days post-challenge

Figure 8:
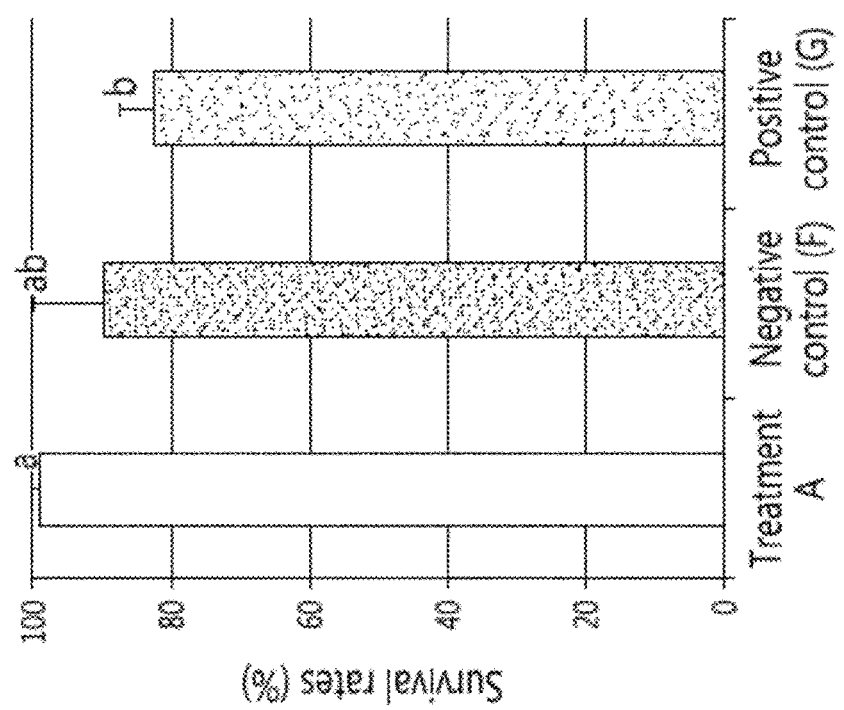
FIG. 8 shows the survival rates of shrimps after 14 days post-challenge (Mean±SD) according to example 6; means indicated with same uppercase letter do not differ between treatments (Fisher's test, 5% probability).

The survival rates of shrimps after 14 days post-challenge are given in FIG. 8 (Mean ±SD) of the treatments; means indicated with same uppercase letter do not differ

| | | EHP-parasite load (copies/g) | | |
|---|---|---|---|---|
| Treatment | Rep. | Day 14 (before challenge) | 48 hours post-challenge | 120 hrs post-challenge |
| Treatment A | 1 | 0E+00 | 7.76E+04 | 0E+00 |
| | 2 | 0E+00 | 1.40E+04 | 0E+00 |
| | 3 | 0E+00 | 3.09E+04 | 0E+00 |
| | 4 | 0E+00 | 3.10E+05 | 0E+00 |
| | 5 | 0E+00 | 1.07E+05 | 1.33E+05 |
| Negative control (F) | 1 | 0E+00 | 0E+00 | 0E+00 |
| | 2 | 0E+00 | 0E+00 | 0E+00 |
| | 3 | 0E+00 | 0E+00 | 0E+00 |
| | 4 | 0E+00 | 0E+00 | 0E+00 |
| | 5 | 0E+00 | 0E+00 | 0E+00 |
| Positive control (G) | 1 | 0E+00 | 3.00E+04 | 3.14E+04 |
| | 2 | 0E+00 | 1.14E+05 | 0E+00 |
| | 3 | 0E+00 | 3.01E+04 | 3.62E+04 |
| | 4 | 0E+00 | 1.43E+04 | 8.69E+04 |
| | 5 | 0E+00 | 9.40E+04 | 1.66E+05 | between treatments (Fisher's test. 5% probability).

The result of the qPCR testing on EHP parasite load is given in table 16. At the beginning of the challenge experiment (right before challenge), there is a free status of EHP in the treatments. After 48 hrs post-challenge, the experiment shrimp in the Treatment A and Positive control (G) are affected with the disease, whereas it was a free status of EHP in the Negative control (F). Hence, this indicates that the trial set up was acceptable and no cross-contamination happened to the Negative control. The EHP parasite load in Treatment A, and G were similar after 48 hours. However after 120 hrs post-challenge, the EHP parasite load in the treatment A was below the detection limit in 4 tanks out of 5 whereas all the tanks from the negative control were positive for EHP (5/5).

Example 7

Evaluation of the effect of 50 SC/CU parietal polysaccharides on the resistance of broilers to heat stress Heat stress is one of the most important environmental stressors challenging poultry production worldwide. Heat stress negatively impacts poultry performance, reducing growth and product safety. During periods of heat stress broiler chicken undergo major thermo-regulation adaptations in order to prevent death due to heat exhaustion and this has a detrimental effect on performance.

Experimental Design

Location: Private Experimental farm (France)

Experimental design: 2 groups:

Control (C): no supplementation; 50 SC/CU PARIETAL POLYSACCHARIDES (Y): 50 SC/CU PARIETAL POLYSACCHARIDES at 800 g/ton and 400 g/ton in starter and grower periods, respectively. No 50 SC/CU PARIETAL POLYSACCHARIDES supplementation during the finishing period (800-400-0).

Diets:

3 phases (starter, grower and finisher). The three feeding phases were: 0-10, 11-25, 26-35 days.

Animals:

Trial was run on broilers of Ross PM3 breedallocated randomly at arrival in 13 pens to reach a density of 20 birds/pen (C: 6 pens, Y: 7 pens).

Heat Stress Challenge:

Heat stress challenge was performed at D20: in the night between D19 and D20, temperature was increased up to 31° C. in the room.

Measurements: Mortality number and dates per pen.

Statistical Analyses:

The difference in mortality between the 2 groups during the trial (and in particular the resistance of birds to heat stress) was analysed by Kaplan-Meier test. Differences between the groups were considered as significant for p-value $p<0.1$. Otherwise statistical analyses appear as not significant (NS).

Results

Mortality and resistance of birds to heat stress challenge: the results are given in table 17

TABLE 17

| Group | Number of birds alive at the end of trial | Total number of dead birds during the trial | Number of dead birds during the heat stress | % total mortality |
|---|---|---|---|---|
| C (n = 6) | 82 | 38 | 31 | 31.7% |
| Y (n = 7) | 123 | 17 | 9 | 12.1% |

40 birds died during the heat stress challenge: 9 birds in the 50 SC/CU PARIETAL POLYSACCHARIDES group and 31 birds in the control group. The overall number of dead birds was 17 in the 50 SC/CU PARIETAL POLYSACCHARIDES group and 38 in the control group. Kaplan-Meier analysis (statistical test comparing the mean survival time in the 2 groups) was strongly significant ($p<0.001$) and gave the following estimation: mean survival time of 29.6 and 32.9 days for C and Y groups, respectively. 50 SC/CU PARIETAL POLYSACCHARIDES group was therefore more resistant to acute heat stress challenge than the control group.

In conclusion, feeding 50 SC/CU PARIETAL POLYSACCHARIDES led to a better resistance to heat stress.

Example 8

Introduction and Objective

The objective of the current trial was to test the effect of 50 SC/CU PARIETAL POLYSACCHARIDES on post-weaning piglets performance, morbidity, and incidence of diarrhea, after removal of medications.

Experimental Design

Animals and Housing

In total, 480 weanling piglets (dam line: Large White× Landrace; sire line: Danbred Duroc) of 4 subsequent batches were distributed in 8 nursery rooms of 4 pens each, in groups of 20 piglets/pen. They were distributed so that initial body weight was as much homogeneous as possible within a pen and among treatments, and placing 10 gilts and 10 males in each pen.

Piglets were vaccinated against *Mycoplasma* at 7 and 21 days of age, and for *Circovirus* at 21 days of age.

Period

Trial took place from weaning at 19 days of age on average, and lasted for 55 days.

Treatments

Piglets were fed a two-phase feeding program, and had free access to feed and water during the whole experimental period There were 2 treatments (table 18): Control (C) and TRIAL 1 (T1).

The antibiotic strategy currently used at the farm is: Prestarter: 120 ppm colistine+300 ppm amoxicillin+2400 ppm ZnO; Starter: 1600 ppm ZnO.

For the trial, with the objective of challenging the piglets, medication became: Prestarter: 2400 ppm ZnO; Starter: blank feed.

TABLE 18

Treatments

| Treatment | Prestarter (days 0-21) | Starter (days 22-55) |
|---|---|---|
| C | Prestarter diet | Starter diet |
| T1 | Prestarter diet + 800 g/t 50 SC/CU PARIETAL POLYSACCHARIDES | Starter diet + 400 g/t 50 SC/CU PARIETAL POLYSACCHARIDES |

Experimental set up and observations

Body weight: individual. At the beginning and at the end of the experiment, and at the change of diet.

Feed intake: per pen. At the change of diet, as the difference between feed supplied and the left over on the day of change.

Morbidity: individual and group health care intervention, including regular herd prophylaxis.

Mortality: date, weight, and apparent reason.

Diarrhoea: per pen. Daily check of diarrhoea incidence.

Statistics

Analysis of variance with the General linear model in SPSS 22.0 (IBM), according to the model:

$$Y_{jk} = \mu + a \times IBW + \text{batch}_j + \text{treatment}_k + \text{batch}_j * \text{treatment}_k + e_{jk}$$

Where:

Y=final body weight (FBW), average daily gain (ADG), average daily feed intake (ADFI), feed conversion ratio (FCR), mortality; IBW=initial body weight used as a covariate; batch=fixed effect caused by batch (j=1,2,3,4); treatment=fixed effect caused by treatment (k=C,T1); batch*treatment=interaction between experimental treatment and batch; e=error. The experimental unit was the pen. Significance was declared from P<0.05.

No interaction was found between treatment and batch. As a consequence, it was removed from the model.

Results

Performance

There were significant differences in FBW (P<0.01), starter and overall growth (P<0.05), and in starter FCR (P<0.05), being the piglets in T1 the ones with a higher BW, faster growth, and lower FCR. Furthermore, T1 piglets tended to grow faster in the starter (P<0.1) and to eat more in the starter (P<0.1). Performance results are shown in table 19.

TABLE 19

Performance results by period and overall of piglets in treatments C and T1

| | CONTROL | T1 | SEM | P value |
|---|---|---|---|---|
| IBW (kg) | 6.40 | 6.40 | 0.089 | — |
| BW prestarter (kg) | 11.33 | 11.63 | 0.123 | 0.101 |
| FBW (kg) | 30.43 | 31.58 | 0.276 | 0.008 |
| ADG prestarter (g/d) | 240 | 255 | 6 | 0.098 |
| ADG starter (g/d) | 581 | 607 | 7 | 0.015 |
| Overall ADG (g/d) | 449 | 470 | 4 | 0.012 |
| ADFI prestarter (g/d) | 350 | 382 | 13 | 0.090 |
| ADFI starter (g/d) | 960 | 963 | 17 | 0.915 |
| Overall ADFI (g/d) | 724 | 737 | 14 | 0.484 |
| FCR prestarter (g/g) | 1.457 | 1.499 | 0.042 | 0.496 |
| FCR starter (g/g) | 1.657 | 1.585 | 0.023 | 0.041 |
| Overall FCR (g/g) | 1.614 | 1.566 | 0.023 | 0.160 |

The fact that the differences are stronger in the starter than in the prestarter period is probably due to the fact that the farm had a good health status, and in the starter period the piglets were more challenged with a blank diet than during the prestarter phase.

Mortality was low during the experimental period, and there were no differences between treatments. On average along the whole period, it was 1.8%. In total, 13 piglets died during the trial.

Conclusions:

The main conclusions of this trial are:

Addition of 50 SC/CU PARIETAL POLYSACCHARIDES in the post-weaning diets improves final body weight, overall average daily gain, and numerically overall feed conversion ratio, respect to a control diet with limited medication.

The impact seems to be stronger in the starter period than in the prestarter period, probably depending on the health status of the farm.

50 SC/CU PARIETAL POLYSACCHARIDES could be a good potential ZnO and/or antibiotics replacer during the starter phase.

It is recommended to test the potential of 50 SC/CU PARIETAL POLYSACCHARIDES to replace antibiotics, comparing a 50 SC/CU PARIETAL POLYSACCHARIDES treatment to a positive control, and the possible complementary effect of the addition of 50 SC/CU PARIETAL POLYSACCHARIDES on top of antibiotics.

Example 9

Facilities, Sample Descriptions and Experimental Diets

The experiment was carried out with Rainbow trout (*Oncorhynchus mykiss*) fingerlings. After four weeks acclimation 480 fish (23.07±0.2 g) were randomly distributed into 16×150-1 fibreglass tanks (30 fish per tank) containing aerated recirculated freshwater. Fish were fed diets to a fixed regime of 3% body weight per day spread across three feeding times (0900, 1300 and 1700 hrs) for 56 days. Fish were batch weighed on bi-weekly basis following a 24 hr starvation period and reared at 14.5±0.5° C. with a 12:12 hr light:dark photoperiod. Water pH was maintained between 6.8-7.5, dissolved oxygen between 7.5-8 mg/l, ammonium between 0.04-0.08 mg/l, nitrite between 0.02-0.06 mg/l and nitrate between 54-58 mg/l. Rainbow trout were fed one of four dietary regimes with quadruplicate tanks for each treatment: 1] control, 2] 60 SC PARIETAL POLYSACCHARIDES, 3] 50 SC/CU PARIETAL POLYSACCHARIDES-continuous fed, and 4] 50 SC/CU PARIETAL POLYSACCHARIDES-pulsed for 56 days (refer to Table 21 for composition of diets).

TABLE 21

Formulation of experimental diets for the Plymouth experiment. Each ingredient component is expressed as g/kg per diet.

|  | Control | 60 SC PARIETAL POLYSACCHARIDES | 50 SC/CU PARIETAL POLYSACCHARIDES |
|---|---|---|---|
| Feed commodity | | | |
| Fishmeal LT94 | 300.0 | 300.0 | 300.0 |
| Soybean meal dehulled | 100.0 | 100.0 | 100.0 |
| SPC60 | 143.0 | 143.0 | 143.0 |
| CGM | 40.0 | 40.0 | 40.0 |
| Vital wheat gluten | 100.0 | 100.0 | 100.0 |
| Fish oil | 82.5 | 82.5 | 82.5 |
| Fat, vegetable | 80.0 | 80.0 | 80.0 |
| Corn starch | 139.5 | 139.5 | 139.5 |
| Vitamin + mineral | 10.0 | 10.0 | 10.0 |
| CMC binder | 5.0 | 5.0 | 5.0 |
| 60 SC PARIETAL POLYSACCHARIDES ™ |  | 4.0 |  |
| 50 SC/CU PARIETAL POLYSACCHARIDES ™ |  |  | 1.5 |
| Proximate analysis (% dry matter basis) | | | |
| Dry matter (%) | 95.8 | 93.9 | 95.6 |
| Crude Protein (%) | 47.2 | 46.1 | 47.4 |
| Crude Lipid (%) | 19.0 | 20.2 | 19.9 |
| Ash (%) | 7.0 | 7.2 | 7.4 |

Methodology

Mucus Collection

Figure 9:
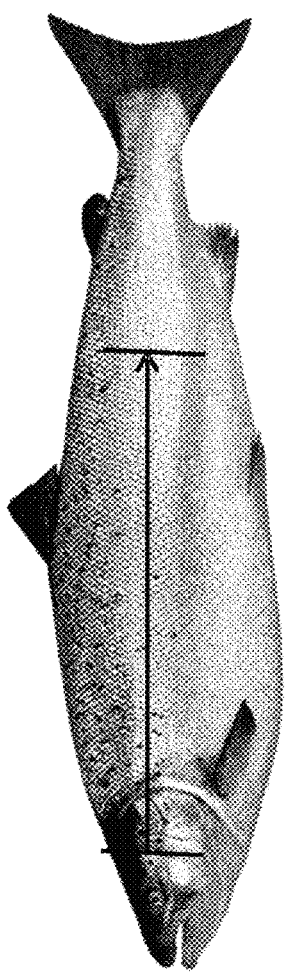
FIG. 9 shows the direction of spatula swipe for Atlantic salmon and Rainbow trout according to example 9.

Fish are to be randomly selected and humanely killed according to trial station protocols. MS222 is the preferred choice of anaesthetic. Caution must be taken when netting fish that this is done as quickly as possible with minimal disruption to the mucosal surfaces of the fish. Immediately following death, mucus is to be collected by scraping one side of the fish using a small spatula from the edge of the operculum to the anus (FIG. 9: Direction of spatula swipe for Atlantic salmon and Rainbow trout). The accumulated mucus at the tail end of the fish is to be transferred into a 1 ml pre weighed syringe. Mucus is stored in 1 ml eppendorf tubes and immediately frozen at −80° C., awaiting analysis.

Real-Time qPCR Sample Collection

Skin samples (<100 mg) were collected from rainbow trout, transferred to 1 mL RNAlater solution (Applied Biosystems, Warrington, UK) and stored at 4° C. for 24 h and then at −80° C. until RNA extraction. Following RNA extraction, a qPCR was applied to look at the expression of a specific biomarker of mucus production.

Growth Performance Calculations

Growth was assessed by weight gain (WG), specific growth rate (SGR), feed conversion ratio (FCR), protein efficiency ratio (PER), condition factor (K). Calculations were made using the following formulae: NWG (g)=FW−IW; SGR (% BW/day)=100 ((ln FW−ln IW)/T); FCR (g/g) =FI/WG; PER=WG/PI; K=FW/(FL$^3$). Where FW=final weight (g), IW=initial weight (g), T=duration of feeding (days), WG=wet weight gain (g), FI=feed intake (g), PI=protein ingested (g) and FL=final length (cm).

Results

Mucus Sample Analysis

The data for mucus production is presented in Table 22. Mucus production was increased in fish fed 60 SC and 50 SC/CU vs control, with a numerical advantage in favour of 50 SC/CU.

TABLE 22

Skin mucus production of fish (mg/cm) after 28 and 56 days of feeding on experimental diets. Data is presented as means ± SD.

| | Treatment | | | |
|---|---|---|---|---|
| | Control | 60 SC PARIETAL POLYSACCHARIDES | 50 SC/CU PARIETAL POLYSACCHARIDES (cont.) | 50 SC/CU PARIETAL POLYSACCHARIDES (pulsed) |
| Day 28 | 50.0 ± 21.5 | 75.0 ± 14.7 | 82.5 ± 22.1 | 65.0 ± 22.0 |
| Day 56 | 66.7 ± 22.0 | 80.8 ± 26.0 | 85.0 ± 27.9 | 83.3 ± 14.7 |

Real-Time qPCR Analysis

Figure 10:
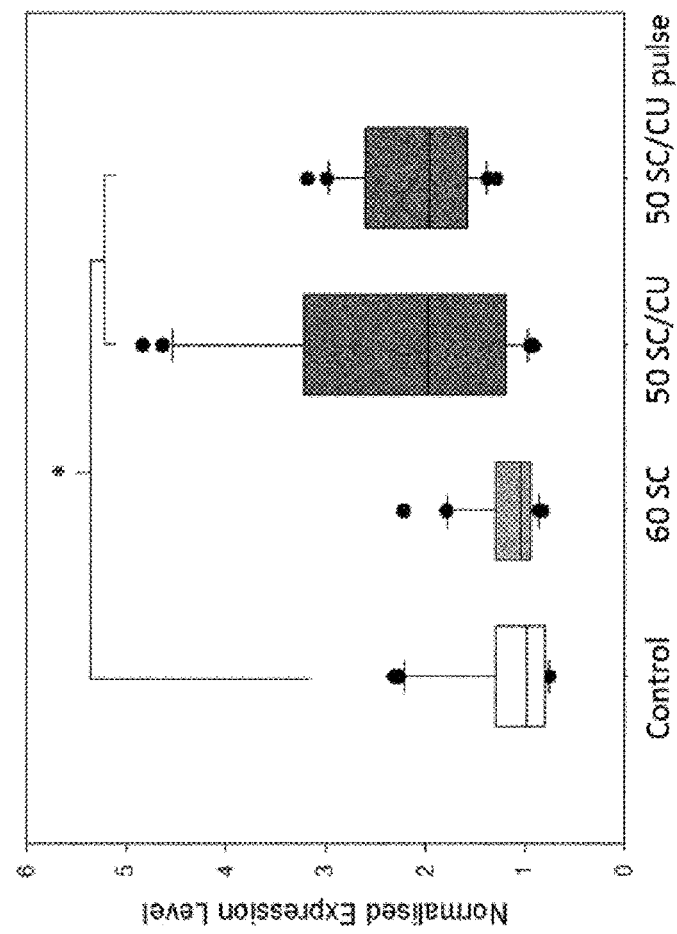
FIG. 10 shows the Relative Expression Levels of gene related to the level of mucus production in skin samples from rainbow trout (*O. mykiss*) fed for 8 weeks on experimental diets supplemented with 60 SC PARIETAL POLYSACCHARIDES and (50 SC/CU PARIETAL POLYSACCHARIDES™) according to example 9. Data presented boxplots (n=10/treatment). *-denotes significant up-regulation; P<0.0001

The gene expression analysis of the skin samples from rainbow trout revealed a significant up-regulation of the expression of a specific biomarker of mucus production in fish fed 50 SC/CU PARIETAL POLYSACCHARIDES diet continuously (2.31±1.26 NEL; P=0.0003) and pulsed (2.09±0.58 NEL; P<0.0001), compared to control fed fish (1.16±0.48 NEL). Data is presented in FIG. 10 which shows the Relative Expression of this gene in skin samples from rainbow trout (*O. mykiss*) fed for 8 weeks on experimental diets supplemented with 60 SC PARIETAL POLYSACCHARIDES and (50 SC/CU PARIETAL POLYSACCHARIDES™). Data presented boxplots (n=10/treatment). *-denotes significant up-regulation; P<0.0001

Growth Performance

Compared to control fed fish, rainbow trout fed the experimental diets for 56 days revealed no significant differences in growth performance. The data is presented in FIG. 11 showing the growth performance of rainbow trout fed experimental diets for 56 days.

Example 10

Fish, Experimental Design and Diet Formulation

After 4 weeks acclimation 225 seabass (15.45±0.1 g) were randomly distributed into 9×110-1 fibreglass tanks (25 fish per tank). The sea bass were fed at a fixed rate of 2.0% of body weight per day spread across 3 feeding times 9:00, 13:00 and 16:30 hr for 10 weeks. Fish were batch weighed weekly following a 24 hr starvation period and reared at 24.14±0.85° C., salinity 26.58±4.32 with a 12:12 hr light: dark photoperiod. Water pH was maintained between 6.8-7.5, dissolved oxygen between 7.5-8 mg/l, ammonium between 0.04-0.08 mg/l, nitrite between 0.02-0.06 mg/l and nitrate between 54-58 mg/l.

Diets were formulated to contain a high inclusion level of soybean meal (40% inclusion), dietary formulation is shown in Table 23.

TABLE 23

Formulation of experimental diets. Each ingredient component is expressed (% inclusion level).

| Feed commodity | Control | 60 SC parietal polysaccharides | 50 SC/CU PARIETAL POLYSACCHARIDES ™ |
|---|---|---|---|
| Fishmeal LT94 | 15.0 | 15.0 | 15.0 |
| Soybean meal dehulled | 38.9 | 38.9 | 38.9 |
| CGM | 16.0 | 16.0 | 16.0 |
| Fish oil | 11.9 | 11.9 | 11.9 |
| Corn starch | 16.6 | 16.6 | 16.6 |
| Vitamin + mineral | 1.0 | 1.0 | 1.0 |
| CMC binder | 0.5 | 0.5 | 0.5 |
| 60 SC parietal polysaccharide ™ | | 0.2 | |
| 50 SC/CU PARIETAL POLYSACCHARIDES ™ | | | 0.08 |

Methodology

Light Microscopy Analysis (LM)

Fish distal intestine was removed, fixed in 10% marine formalin and kept at 4° C. for 48 hours, and subsequently transferred to 70% ethanol for storage. Prior to analysis intestinal samples were dehydrated (Leica TP 1020) and embedded in paraffin wax according Dimitriglou et al (Journal of animal science, 2009, 87, 3226-3234).

Samples were sectioned at 5 µm thickness (Leica RM2235 microtome), dried in an oven overnight and thereafter auto-stained with haematoxylin and eosin (HE) (Leica Autostainer XL). Slides were mounted with cover slips using DPX and left to dry. Photographs of stained samples were then captured (Leica DMIRB microscope and Olympus E410 digital SLR camera). Image analysis was conducted using Image J 1.47v (National institutes of Health, Bethesda, Md., USA) software. LM images were used to calculate fold length (FL) and lamina propria width (LP-W), in addition to goblet cell (GC) and measured over 200 µm. For perimeter ratios (PR), the image threshold was adjusted, following conversion to 8-bit. The inside perimeter was divided by the outside perimeter to calculate the ratio. Data are presented as mean±standard deviation (SD) and statistical analysis was conducted using SPSS statistics version 15 for windows (SPSS Inc., Ill., USA) and accepted at P<0.05. Histological data was analysed using one-way ANOVA. Significant differences between control and treatment groups were determined using post-hoc Tukey's HSD test.

Scanning Electron Microscopy (SEM)

Figure 13:
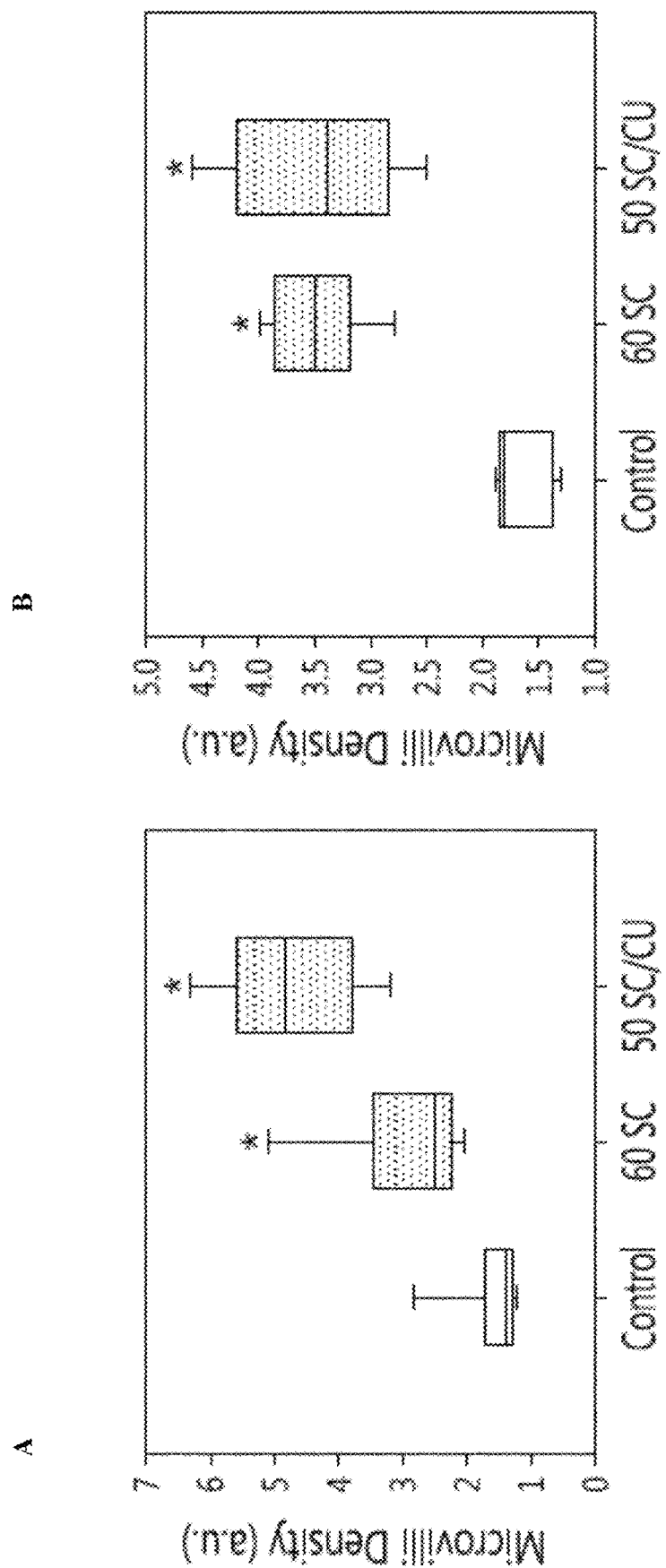
FIG. 13 illustrates the microvilli density measurements of the posterior intestine of seabass fed control and experimental diets for (13A) 5 weeks and (13B) 10 weeks according to example 10. Asterisks denote a significant difference between control diet fed fish and fish fed experimental diet (P<0.001).

Samples were fixed in 2.5% glutaraldehyde with 0.1 M sodium cacodylate buffer (1:1 vol., pH 7.2). Samples were then dehydrated in a graded ethanol series (30% alcohol, 50%, 70%, 90% and 100% x2) for 15 min at each step and critical point dried (K850 Emitech) with ethanol as the intermediate fluid and $CO_2$ as the transition fluid. The samples were then sputter coated (K550 Emitech) with gold and viewed with a JSM 6610 LV scanning electron microscope. For each sample, multiple images were captured at magnifications ranging from x500-x 20,000 to assess general intestinal integrity. Microvilli density measurements were conducted using Image J (V1.45) using images at x 20,000 magnification (FIG. 13). SEM data was analysed using one-way ANOVA. Significant differences between control and treatment groups were determined using post-hoc Tukey's HSD test.

Real-Time qPCR Sample Collection

Posterior intestinal samples (<100 mg) were collected from. European seabass, transferred to 1 mL RNAlater solution (Applied Biosystems, Warrington, UK) and stored at 4° C. for 24 h and then at −80° C. until RNA extraction.

RNA Extraction and cDNA Synthesis

Total RNA was extracted using TRI reagent (Ambion, Life technologies, UK) according to the manufacturer's instructions, with some modifications. Briefly, 50-100 mg intestinal samples were removed from the RNAlater solution and excess solution was removed by pressing the sample between sterile tissue. The samples (<100 mg) were transferred into a tube containing 1 mL TRI reagent and homogenised for 10 min. Following this 200 µl of chloroform was added and after mixing, samples were centrifuged at 12,000×g for 15 min. The upper aqueous phase was transferred into a tube containing an equal volume of isopropanol. Mixtures were vortexed and centrifuged at 14,000×g for 15 min. Supernatants were discarded and the precipitated RNA pellets were washed using 1 ml of 75% ethanol. Total RNA was dissolved in diethylpyrocarbonate (DEPC) and to remove any contaminating genomic DNA were purified using RNeasy Plus Mini Kit according to the manufacturer's instructions (Qiagen, UK). The concentration and quality of RNA in each sample were determined by measuring 260/280 nm and 260/230 absorbance ratios (NanoDrop Technologies, Wilmigton, USA). The integrity of RNA was confirmed by running samples on the Bio-analyser, RNA integrity numbers (RIN) ranged from 8.0-9.5 (Agilent technologies, UK), samples were stored at −80 ° C. A total amount of 1 µg of RNA was used for cDNA synthesis, employing iScript cDNA synthesis kit (Bio-Rad, UK). The reaction was placed at 25° C. for 5 min, then 42° C. for 30 min and inactivated at 85° C. for 5 min. The iScript cDNA synthesis kit contains a combination of oligo dTs and random hexamers to work with a wide variety of targets.

Real-Time PCR Assay

PCR reactions were performed with SYBR green method using a StepOne Plus™ Real time-PCR thermal cycler (Applied. Biosystems). Duplicate PCR reactions were carried for each sample analysed. Each PCR reaction was set on a 384 well plate by mixing 2 µl of diluted (1/10) cDNA with 5.5 µl 2 × concentrated iQ™ SYBR Green Supermix (Bio-Rad), containing SYBR Green as a fluorescent intercalating agent, 0.3 µM forward primer and 0.3 µM reverse primer. The primer used and their sequences are presented in Table 1. The thermal profile for all reactions was 10 min at 95° C. and then 40 cycles of 15 s at 95° C., 60 s at 59° C. Florescence monitoring occurred at the end of each cycle. Additional dissociation curve analysis was performed and showed in all cases one single peak. β-actin and GAPDH were used as reference genes in each sample in order to standardise the results by eliminating variation in mRNA and cDNA quantity and quality (Bustin et al., 2009). Indeed, the stability and suitability of GAPDH and β-actin as reference genes were confirmed according to the algorithms used by geNorm™ software (Vandesompele et al., Genome biology, 2002, 3(7), research 0034).

An expression stability value 'M' was generated for each reference gene. No amplification product was observed in negative controls and no primer-dimer formations were observed in the control templates. Modification of gene expression is represented with respect to the controls being sampled at the same time as the treatment.

The threshold cycle (Ct), defined as the point at which the fluorescence rises appreciably above the background fluorescence, was determined manually for each run. PCR efficiencies for each set of primers were determined using serial dilutions of cDNA (n=3) and resulting plots of Ct versus the logarithmic cDNA input, using the equation E (PCR efficiency)=10(−1/slope). The normalised expression level (NEL) of target genes were calculated on the basis of Ct deviation (ΔCt) of the unknown sample versus a control sample, and expressed in comparison to the reference genes GAPDH and β-actin according to calculations outlined by geNorm™ manual hypertext transfer protocol medgen.u-gent.be/~jvdesomp/genorm/) and Vandesompele et al. (Genome biology, 2002, 3(7), research 0034.

All statistics for RT-qPCR data were carried out using permutation test in R.

Growth Performance Calculations

Growth was assessed by weight gain (WG), specific growth rate (SGR), feed conversion ratio (FCR), protein efficiency ratio (PER), condition factor (K). Calculations were made using the following formulae: NWG (g)=FW−IW; SGR (% BW/day)=100 ((ln FW−ln IW)/T); FCR (g/g) =FI/WG; PER=WG/PI; K=FW/(FL$^3$). Where FW=final weight (g), IW=initial weight (g), T=duration of feeding (days), WG=wet weight gain (g), FI=feed intake (g), PI=protein ingested (g) and FL=final length (cm).

Results

Light Microscopy

Figure 12:
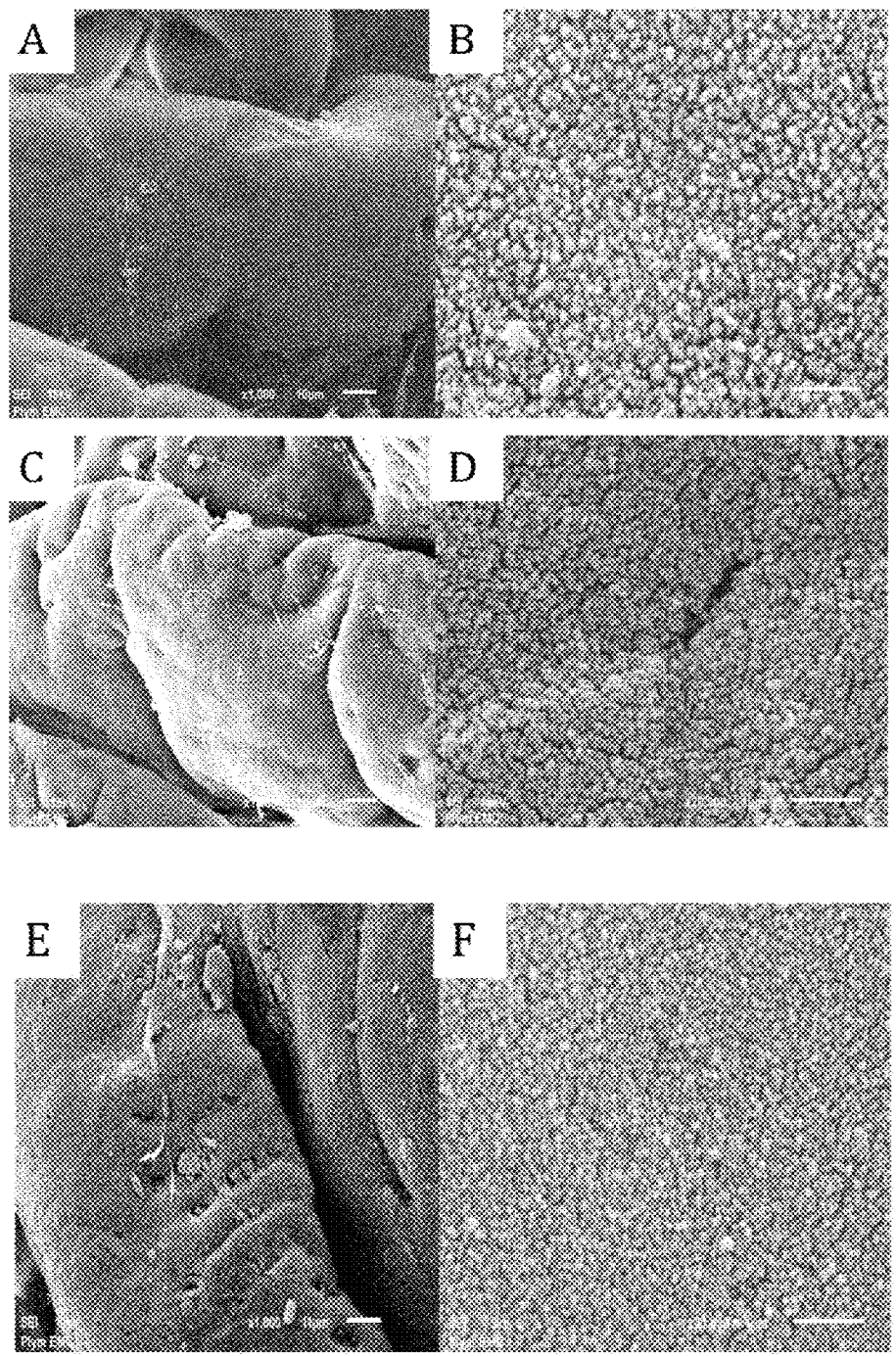
FIG. 12 shows examples of the intestine of seabass fed the control (A&B), 60 SC parietal polysaccharides (C&D), 50 SC/CU PARIETAL POLYSACCHARIDES (E&F) and for 10 weeks according to example 10. Scale bars are 10 μm (images A, C & E) and 1 μm (images B, D & F).

Light microscopy revealed that seabass fed the control and experimental diets showed an intact epithelial barrier and a mucosal arrangement of organised villi-like mucosal folds. The intestinal mucosa consisted of a simple epithelium and lamina propria (LP) which comprised of scattered IELs (see FIG. 12A). The perimeter ratio compared to fish fed control diet (a higher perimeter ratio indicates a higher absorptive intestinal surface brought about by more numerous and/or longer mucosal folds), was significantly elevated in fish fed 50 SC/CU PARIETAL POLYSACCHARIDES diets at both week 5 and 10 of the experimental period (see Table 24A & B). In contrast compared to control fed fish, fish fed the 60 SCPARIETAL POLYSACCHARIDES dietary regime showed a significant elevation in PR only after 10 weeks of feeding (see Table 24B).

TABLE 24A

Light microscopy data after 5 weeks of feeding on experimental diets.

|  | Control | 50 SC/CU PARIETAL POLYSACCHARIDES | 60 SC PARIETAL POLYSACCHARIDES | P-value |
| --- | --- | --- | --- | --- |
| PR | 3.00 ± 0.4$^a$ | 3.60 ± 0.4$^b$ | 3.23 ± 0.4$^{ab}$ | 0.04 |
| FL | 324.59 ± 106.5 | 383.65 ± 146.6 | 334.83 ± 98.7 | 0.55 |
| LP-W (µm) | 13.87 ± 5.2$^a$ | 15.63 ± 4.6$^{ab}$ | 20.10 ± 6.6$^b$ | 0.04 |
| GC | 17.16 ± 6.8 | 9.16 ± 1.5 | 11.16 ± 3.4 | 0.12 |
| IELs | 4.5 ± 1.0 | 8.33 ± 3.4 | 9.33 ± 4.2 | 0.16 |

Data is presented as mean ± standard deviation (n = 6/treatment).
$^{a\text{-}b}$Superscripts denote significant difference using Tukey's HSD post- hoc test

TABLE 24B

Light microscopy data after 10 weeks of feeding on experimental diets.

|  | Control | 50 SC/CU PARIETAL POLYSACCHARIDES polysaccharides ™ | 60 SC PARIETAL POLYSACCHARIDES | P-value |
| --- | --- | --- | --- | --- |
| PR | 3.21 ± 0.1$^a$ | 4.28 ± 0.3$^b$ | 4.15 ± 0.4$^b$ | 0.02 |
| FL | 317.99 ± 74.6$^a$ | 391.31 ± 77.0$^b$ | 336.87 ± 96.0$^{ab}$ | 0.02 |
| LP-W (µm) | 17.95 ± 6.9 | 15.22 ± 4.8 | 18.57 ± 5.4 | 0.28 |

TABLE 24B-continued

Light microscopy data after 10 weeks of feeding on experimental diets.

|  | Control | 50 SC/CU PARIETAL POLYSACCHARIDES polysaccharides ™ | 60 SC PARIETAL POLYSACCHARIDES | P-value |
|---|---|---|---|---|
| GC | 10.33 ± 3.4 | 14.33 ± 6.9 | 13.0 ± 3.8 | 0.65 |
| IELs | 8.83 ± 4.9 | 12.50 ± 4.0 | 9.66 ± 3.5 | 0.20 |

Data is presented as mean ± standard deviation (n = 18/treatment).
[a-b]Superscripts denote significant difference using Tukey's HSD post- hoc test SEM Analysis The epithelial surfaces of all fish appeared to be healthy with uniform enterocyte formations and densely packed microvilli with no signs of cell or microvilli disruption or necrosis. Representative images of fish within each treatment are presented in FIG. 12 and microvilli density measurement analyses are presented in FIGS. 13A and 13B. After 5 weeks of feeding experimental diets (see FIG. 13A), compared to control fed fish (1.58±0.5 a.u.), fish fed 60 SC parietal polysaccharides (2.90±1.0 a.u.) and 50 SC/CU PARIETAL POLYSACCHARIDES (4.81±1.0 a.u.) revealed a significant elevation in microvilli density (P<0.001). Likewise after 10 weeks of feeding the experimental diets (see FIG. 13B), fish fed 60 SC parietal polysaccharides (3.51±0.4 a.u.) and 50 SC/CU PARIETAL POLYSACCHARIDES (3.48±0.7 a.u.) exhibited a significant elevation (P<0.001) in microvilli density compared to fish fed the control diet (1.66±0.2).

Real-Time qPCR

Figure 14:
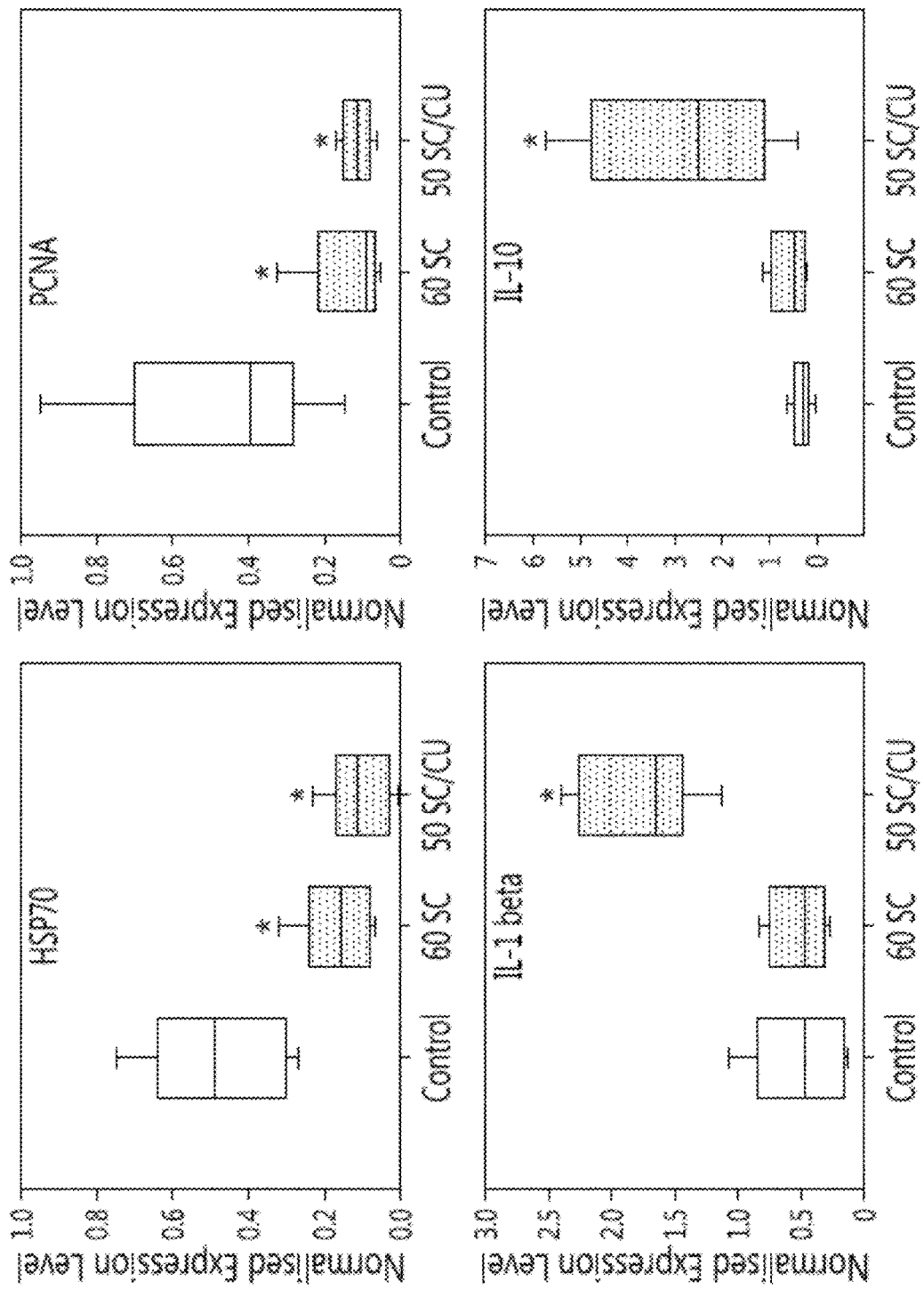
FIG. 14 illustrates the gene expression data for seabass posterior intestinal samples after 10 weeks of feeding on experimental diets. Boxplots show data for HSP70, PCNA, IL-1beta and IL-10 according to example 10. Asterisks denote a significant up or down regulation in gene expression compared to the control fed fish (P<0.05).

The gene expression data revealed that compared to control fed fish (0.48±0.15 NEL), fish fed 60 SC parietal polysaccharides (0.17±0.07 NEL) and 50 SC/CU PARIETAL POLYSACCHARIDES (0.11±0.08 NEL) diets exhibited a significant down (P=0.03) regulation for heat shock protein 70 (HSP70). Likewise for proliferating cell nuclear antigen (PCNA) gene expression fish fed 60 SC parietal polysaccharides (0.14±0.1 NEL) and 50 SC/CU PARIETAL POLYSACCHARIDES (0.12±0.04 NEL) exhibited a significant down regulation (P=0.03) compared to fish fed the control diet (0.47±0.14 NEL). In contrast the gene expression data for the inflammatory effector cytokine interleukin-1beta (IL-1beta) revealed that fish fed 50 SC/CU PARIETAL POLYSACCHARIDES diet (1.74±0.4 NEL) exhibited a significant up-regulation (P=0.03) compared to fish fed control diet (0.51±0.4 NEL). Similarly the gene expression data for the anti-inflammatory effector cytokine interleukin-10 (IL-10) revealed that fish fed the 50 SC/CU PARIETAL POLYSACCHARIDES diet (2.79±2.0 NEL) exhibited a significant up-regulation (P=0.05) compared to fish fed control diet (0.36±0.2 NEL). All data is presented in FIG. 14.

Example 11

Anticoccidial Efficacy of 50 SC/CU parietal polysaccharides in commercial broiler chickens exposed to a mixed challenge of *Eimeria acervulina, E. maxima*, and *E. tenella*

Objective

The objective of the study was to measure the anticoccidial efficacy/sensitivity of 50 SC/CU parietal polysaccharides against a mixture of *Eimeria acervulina, E. maxima*, and *E. tenella*.

Experimental Design

The study consisted of 45 cages starting with 10 chicks each. The eight treatments were replicated nine times.

Treatments

Experimental Design

| Trt | Treatment/Dosage (lbs/ton of feed) | Infected/Non-Infected | Cages/Trt | Birds/Cage |
|---|---|---|---|---|
| 1 | Control: Nonmedicated (NMNI) | NI | 9 | 10 |
| 2 | Negative control: Nonmedicated and infected (NMI) | I | 9 | 10 |
| 6 | 50 SC/CU dose 1 (dose 0.4 X) | I | 9 | 10 |
| 7 | 50 SC/CU dose 2 (dose 1X) | I | 9 | 10 |
| 8 | 50 SC/CU dose 3 (dose 3Xg) | I | 9 | 10 |

Animals

Day of hatch male broiler chicks (strain Ross 708) was used for this trial. At the hatchery, the birds were sexed and received routine vaccinations. Only healthy appearing chicks were used in the study. The study began when the birds were placed (Day 0) at which time they were allocated to the experimental cages. No birds were replaced during the course of the study. Birds were weighed by cage on Days 0, 14, 20, and 28.

Housing

Upon arrival, chicks were placed in battery cages. The floor space per animal was 0.51 sq. ft/bird. Thermostatically controlled gas furnace/air conditioner maintained uniform temperature. Even, continuous illumination was provided by fluorescent lamps hung vertically along the wall. Feed and water were provided ad libitum.

Organism Agent

The coccidial inoculum consisted of a mixed culture of three species of *Eimeria*. The species were *E. acervulina, E. maxima*, and *E. tenella*. The coccidial inoculum was administered by oral gavage to the birds in the infected treatments.

On Day 14 of the study each bird in the noninfected treatment received 1 ml of distilled water by oral pipette (p.o.). Birds in the infected treatments received the coccidial inoculum diluted to a 1 ml volume (p.o.) titrating at an average oocysts count of 75,000, 25,000 and 50,000 for *E. acervulina, E. maxima*, and *E. tenella*, respectively.

Lesion Scoring

On Day 20, five (5) birds per cage were humanely euthanized, and group weighed. Birds were scored for coccidiosis lesion scoring according to the infected region(s) of the intestine.

Challenge Schedule

D14: coccidiosis challenge=75,000, 25,000 and 50,000 for *E. acervulina, E. maxima*, and *E. tenella*, respectively D20: oocysts count in fecal material (mixed per cage) intestinal lesion scoring (5 birds/cage)

Results

Figure 15:
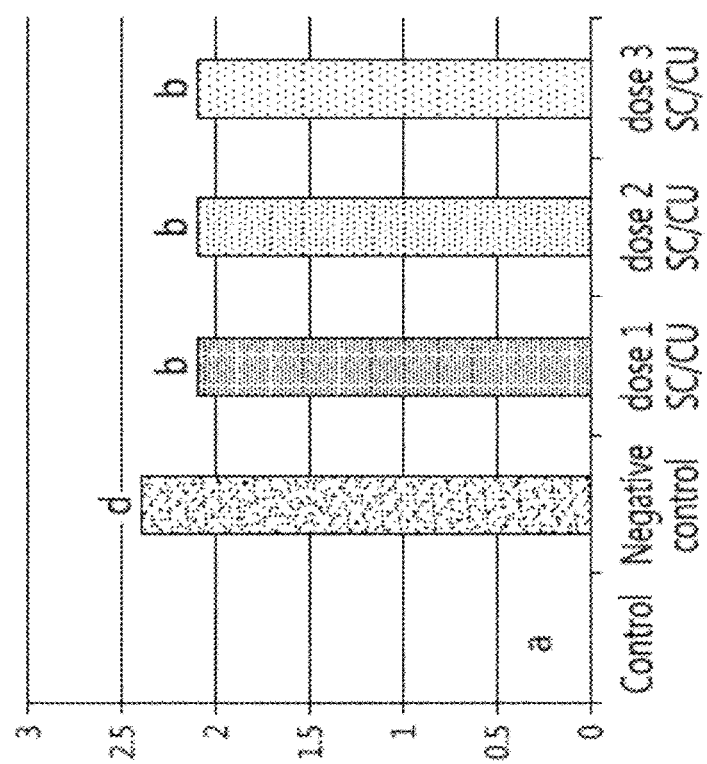
FIG. 15 shows the average intestinal lesion scoring of broiler chicken challenged by *Eimeria acervulina, E. maxima,* and *E. tenella* on day 20 (6 day post challenge) according to example 11.
Figure 16:
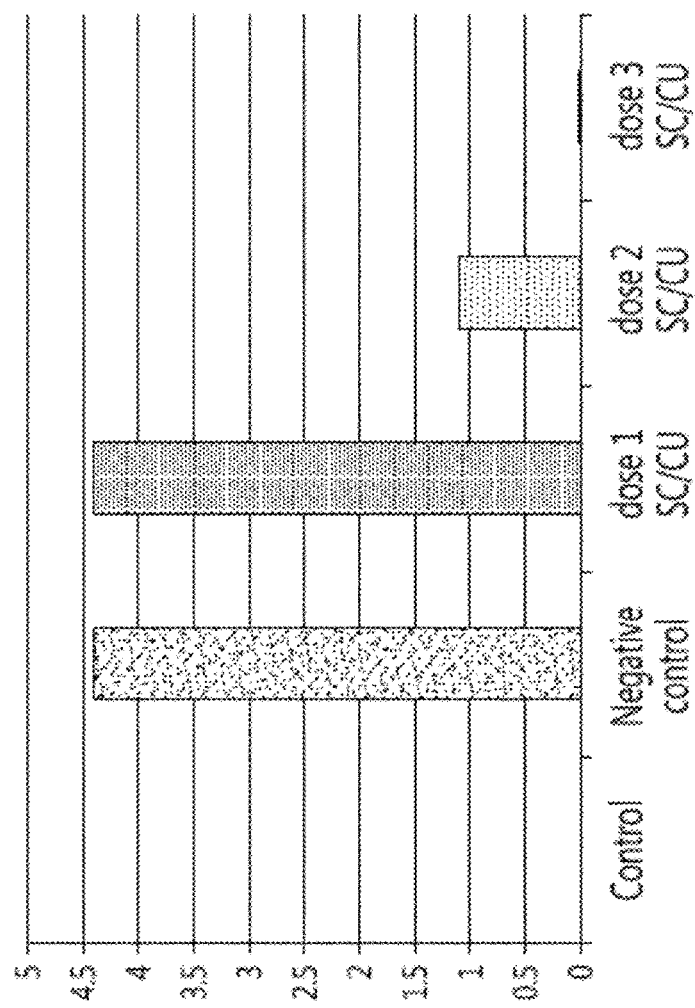
FIG. 16 shows the cumulated mortality of broiler chicken at the end of the trial (in %) according to example 11.
Figure 17:
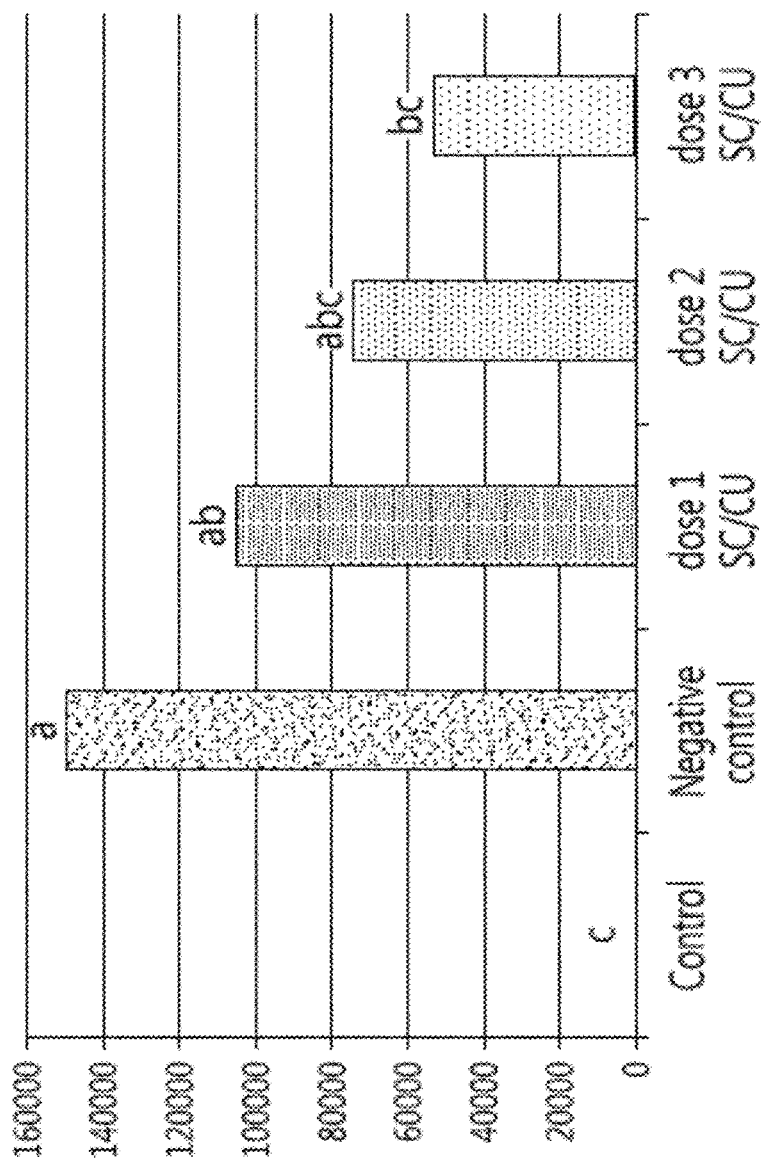
FIG. 17 shows the oocysts fecal excretion (occidia Oocysts per Gram Fecal Material (OPG)) of broiler chicken challenged by *Eimeria acervulina, E. maxima,* and *E. tenella* on day 20 (6 day post challenge) according to example 11.

They are given in FIGS. 15 to 17

As shown in FIG. 15, animals fed 50 SC/CU parietal polysaccharides Showed lower specific lesions associated to *Eimeria acervulina, E. maxima,* and *E. tenella* infection. This effect resulted in a significant lower average lesion scoring.

Interestingly mortality of broiler chicken infected by *Eimeria* sp. over the course of the experiment was also numerically reduced in a dose dependent manner as shown in FIG. 16.

Fecal excretion of pathogens oocysts at day 20 (6 days post infection) was significantly reduced in birds fed 50 SC/CU parietal polysaccharides in a dose dependent manner as showns in FIG. 17.

These results support the fact that feeding broiler chicken wth 50 SC/CH parietal polysaccharides can mitigate the negative effects associated to an infection with *Eimeria* sp.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and as may be applied to the essential features hereinbefore set forth, and as follows in the scope of the appended claims.

The invention claimed is:

1. A composition comprising parietal polysaccharides from at least one *Candida* species and parietal polysaccharides from at least one *Saccharomyces* species, wherein the parietal polysaccharides from the at least one *Candida* species and the parietal polysaccharides from at least one *Saccharomyces* species are chitin, mannan-oligosaccharides, Beta-1,3 glucans and Beta-1,6 glucans in an amount ranging from 20 to 80 weight percent based on the total weight of the composition and wherein the parietal polysaccharides from the at least one *Candida* species are in an amount ranging from 10 to 50 dry weight percent based on the total weight of the parietal polysaccharides in the composition.

2. The composition according to claim 1, wherein the parietal polysaccharides from the at least one *Candida* species are in an amount ranging from 10 to 15 dry weight percent based on the total weight of the parietal polysaccharides in the composition.

3. The composition according to claim 1, wherein the parietal polysaccharides from the at least one *Candida* species are in an amount of at least 10, 15, 20, 25, 30, 35, 40, 45 or 50 dry weight percent based on the total weight of the parietal polysaccharides in the composition.

4. The composition according to claim 2, wherein the parietal polysaccharides from the at least one *Candida* species are in an amount of at least 10, 11, 12, 13, 14 or 15 dry weight percent based on the total weight of the parietal polysaccharides in the composition.

5. The composition according to claim 1, wherein the parietal polysaccharides from the at least one *Candida* species and the parietal polysaccharides from the at least one *Saccharomyces* species are in an amount ranging from 30 to 60 weight percent based on the total weight of the composition.

6. The composition according to claim 1, wherein the parietal polysaccharides from the at least one *Candida* species and the parietal polysaccharides from the at least one *Saccharomyces* species are in an amount of at least 20, 23, 25, 27, 30, 33, 35, 37, 40, 43, 45, 47, 50, 53, 55, 57, 60, 63, 65, 67, 70, 73, 75, 77 or 80 weight percent based on the total weight of the composition.

7. The composition according to claim 1, wherein the parietal polysaccharides from the at least one *Candida* species and the parietal polysaccharides from the at least one *Saccharomyces* species are in an amount of at least 20, 23, 25, 27, 30, 33, 35, 37, 40, 43, 45, 47, 50, 51, 52, 53, 54, 55, 56, 57, 58, 59 or 60 weight percent based on the total weight of the composition.

8. The composition according to claim 1, wherein the parietal polysaccharides from the at least one *Candida* species are in an amount ranging from 10 to 50 dry weight percent based on the total weight of the parietal polysaccharides in the composition; and the parietal polysaccharides from the at least one *Candida* species and the parietal polysaccharides from the at least one *Saccharomyces* species are in an amount ranging from 30 to 60 weight percent based on the total weight of the composition.

9. The composition according to claim 1, wherein the parietal polysaccharides from the at least one *Candida* species are in an amount of at least 10, 15, 20, 25, 30, 35, 40, 45 or 50 dry weight percent based on the total weight of the parietal polysaccharides in the composition; and the parietal polysaccharides from the at least one *Candida* species and the parietal polysaccharides from the at least one *Saccharomyces* species are in an amount ranging from 30 to 60 weight percent based on the total weight of the composition.

10. The composition according to claim 1, wherein the parietal polysaccharides from the at least one *Candida* species are in an amount ranging from 10 to 50 dry weight percent based on the total weight of the parietal polysaccharides in the composition; and the parietal polysaccharides from the at least one *Candida* species and the parietal polysaccharides from the at least one *Saccharomyces* species are in an amount of at least 30, 31, 32, 33, 34, 35, 36, 37, 38, 39, 40, 41, 42, 43, 44, 45, 46, 47, 48, 49, 50, 51, 52, 63, 54, 55, 56, 57, 58, 59 or 60 weight percent based on the total weight of the composition.

11. The composition according to claim 1, wherein the parietal polysaccharides from the at least one *Candida* species are in an amount of at least 10, 15, 20, 25, 30, 35, 40, 45 or 50 dry weight percent based on the total weight of the parietal polysaccharides in the composition; and the parietal polysaccharides from the at least one *Candida* species and the parietal polysaccharides from the at least one *Saccharomyces* species are in an amount of at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 weight percent based on the total weight of the composition.

12. The composition according to claim 1, wherein the at least one *Candida* species is *Candida utilis*.

13. The composition according to claim 1, wherein the parietal polysaccharides from the at least one *Saccharomyces* species are from *Saccharomyces cerevisiae* sp.

14. The composition according to claim 1, for use in modulating and/or stimulating immune responses in an animal.

15. The composition according to claim 1, wherein the at least one *Saccharomyces* species is *Saccharomyces cerevisiae* and the at least one *Candida* species is *Candida utilis* and wherein the parietal polysaccharides from the at least one *Saccharomyces cerevisiae* are in an amount ranging from 30 to 50 weight percent based on the total weight of the composition and wherein the parietal polysaccharides from the *Candida utilis* are in an amount ranging from 5 to 15 weight percent based on the total weight of the composition.

\* \* \* \* \*